(12) United States Patent
Eisenbach-Schwartz et al.

(10) Patent No.: US 9,089,509 B2
(45) Date of Patent: Jul. 28, 2015

(54) METHOD OF TREATMENT OF AGE-RELATED MACULAR DEGENERATION

(75) Inventors: Michal Eisenbach-Schwartz, Rehovot (IL); Oleg Butovsky, Beer Sheva (IL)

(73) Assignee: YEDA RESEARCH AND DEVELOPMENT CO., LTD., Rehovot (IL)

(*) Notice: Subject to any disclaimer, the term of this patent is extended or adjusted under 35 U.S.C. 154(b) by 1252 days.

(21) Appl. No.: 12/308,880

(22) PCT Filed: Jun. 28, 2007

(86) PCT No.: PCT/IL2007/000798
§ 371 (c)(1),
(2), (4) Date: Jun. 16, 2009

(87) PCT Pub. No.: WO2008/001380
PCT Pub. Date: Jan. 3, 2008

(65) Prior Publication Data
US 2010/0135953 A1    Jun. 3, 2010

Related U.S. Application Data

(60) Provisional application No. 60/806,041, filed on Jun. 28, 2006.

(51) Int. Cl.
| | | |
|---|---|---|
| *A61K 38/16* | (2006.01) | |
| *A61K 38/02* | (2006.01) | |
| *A61K 38/07* | (2006.01) | |
| *A61K 35/12* | (2006.01) | |
| *A61K 39/00* | (2006.01) | |
| *A61K 35/17* | (2015.01) | |
| *A61K 35/15* | (2015.01) | |
| *A61K 38/10* | (2006.01) | |
| *A61K 38/20* | (2006.01) | |
| *C07K 5/10* | (2006.01) | |
| *C07K 7/00* | (2006.01) | |
| *C07K 14/00* | (2006.01) | |
| *C12N 5/0783* | (2010.01) | |
| *C07K 14/54* | (2006.01) | |

(52) U.S. Cl.
CPC ............ *A61K 39/0007* (2013.01); *A61K 35/15* (2013.01); *A61K 35/17* (2013.01); *A61K 38/10* (2013.01); *A61K 38/16* (2013.01); *A61K 38/2026* (2013.01); *C07K 5/10* (2013.01); *A61K 35/12* (2013.01); *A61K 38/02* (2013.01); *A61K 38/07* (2013.01); *C07K 7/00* (2013.01); *C07K 14/5406* (2013.01); *C12N 5/0636* (2013.01)

(58) Field of Classification Search
None
See application file for complete search history.

(56) References Cited

U.S. PATENT DOCUMENTS

| 6,844,314 B2 | 1/2005 | Eisenbach-Schwartz et al. |
|---|---|---|
| 2003/0004099 A1 | 1/2003 | Eisenbach-schwartz |
| 2003/0149997 A1 | 8/2003 | Hageman |
| 2004/0092435 A1 | 5/2004 | Peyman |
| 2004/0248802 A1 | 12/2004 | Eisenbach-Schwartz et al. |
| 2005/0118180 A1 | 6/2005 | Rubinfeld |
| 2005/0220803 A1 | 10/2005 | Eisenbach-Schwartz |
| 2006/0057110 A1 | 3/2006 | Eisenbach-Schwartz |
| 2007/0248569 A1* | 10/2007 | Eisenbach-Schwartz et al. ............ 424/85.2 |
| 2009/0214470 A1* | 8/2009 | Eisenbach-Schwartz et al. ............ 424/85.2 |

FOREIGN PATENT DOCUMENTS

| WO | 03079968 A2 | 10/2003 |
|---|---|---|
| WO | WO 03/105750 A2 * | 12/2003 |
| WO | 2004060265 A2 | 7/2004 |

OTHER PUBLICATIONS

Landa et al. Weekly vaccination with Copaxone (glatiramer acetate) as a potential therapy for dry age-related macular degeneration. Curr Eye Res 33: 1011-1013, 2008.*
Landa et al. Qualitative spectral OCT/SLO analysis of drusen change in dry age-related macular degeneration patients treated with Copaxone. J Ocular Pharmacol Therapeutics 27: 77-82, 2011.*
Klaver et al. Is Age-related maculopathy associated with Alzheimer's disease? The Rotterdam Study. Am J Epidem 150(9): 963-968, 1999.*
Nowak, J.Z. Age-related macular degeneration (AMD): pathogenesis and therapy. Pharmacol Reports 58: 353-363, 2006.*
Olejnik et al. Drug delivery strategies to treat age-related macular degeneration. Advanced Drug Delivery Rev 57: 1991-1993, 2005.*

* cited by examiner

*Primary Examiner* — Bridget E Bunner
(74) *Attorney, Agent, or Firm* — Browdy and Neimark, PLLC

(57) ABSTRACT

The invention provides methods and compositions for treatment of age-related macular degeneration, which comprises causing T cells that produce IL-4 to accumulate in the eye by administration of an agent such as Copolymer-1, IL-4, cells activated with IL-4, IL-13 or up to 20 ng/ml IFN-g, or a pathogenic self-antigen associated with a T-cell-mediated specific autoimmune disease of the eye or a peptide derived therefrom, and any combination of such agents.

4 Claims, 15 Drawing Sheets
(1 of 15 Drawing Sheet(s) Filed in Color)

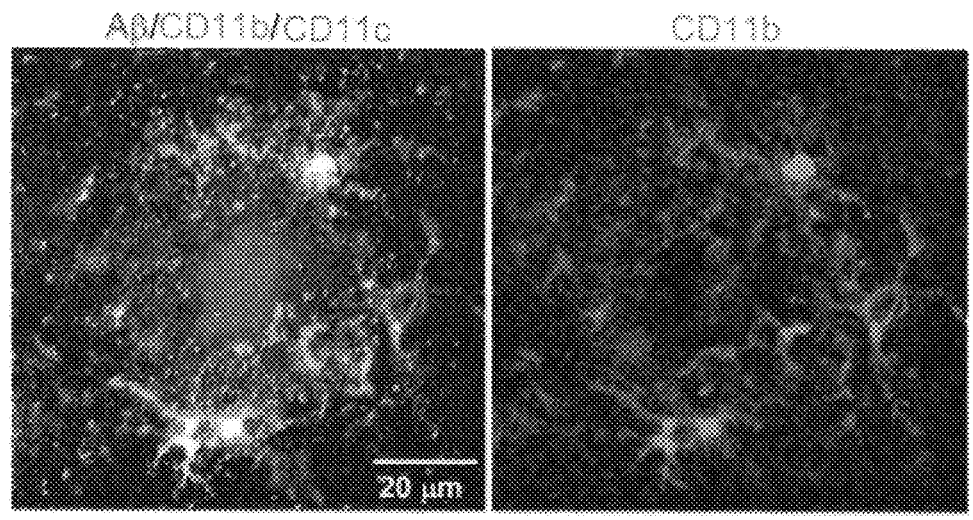
Fig. 3A
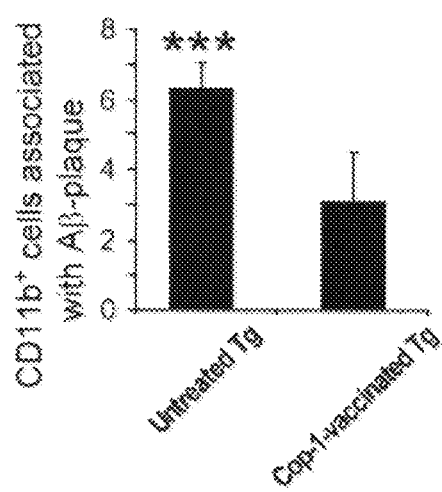 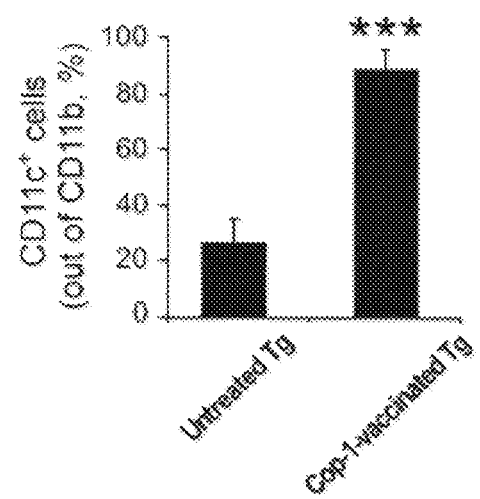
Fig. 3B                              Fig. 3C

METHOD OF TREATMENT OF AGE-RELATED MACULAR DEGENERATION

FIELD OF THE INVENTION

The present invention relates to methods and compositions for treatment of age-related macular degeneration.

Abbreviations: Aβ, amyloid β-peptide; AD, Alzheimer's disease; AMD, age-related macular degeneration; APCs, antigen-presenting cells; BrdU, 5-bromo-2'-deoxyuridine; CNS, central nervous system; COP-1, copolymer 1; GFP, green fluorescent protein; IB-4, *Bandeiraea simplicifolia* isolectin B4; IGF, insulin-like growth factor; IL; interleukin; MG, microglia; MHC-II, class II major histocompatibility complex; MWM, Morris water maze; NPCs, neural stem/progenitor cells; RGCs, retinal ganglion cells; Tg, transgenic; Th, T-helper; TNF-α, tumor necrosis factor-α.

BACKGROUND OF THE INVENTION

Age-Related Macular Degeneration

Age-related macular degeneration (AMD) is a disease affecting the macular region of the eye, which is the area in the retina where the sharp vision is obtained. Macular degeneration is caused by the deterioration of the central portion of the retina, the inside back layer of the eye that records the images we see and sends them via the optic nerve from the eye to the brain. The retina's central portion, known as the macula, is responsible for focusing central vision in the eye, and it controls our ability to read, drive a car, recognize faces or colors, and see objects in fine detail.

AMD is the leading cause of irreversible blindness among the elderly in industrialized nations, and its prevalence increases in the population over the age of 60 (Klein et al., 1992; Mitchell et al., 1995). Numerous attempts have been made to understand the etiology of the disease, its pathophysiology and factors involved in the progression of the disease. A common early sign of AMD is the buildup of drusen, tiny yellow or white fat globules and extracellular material in the retina of the eye or on the optic nerve head. Drusen occurs as hard drusen (small, solid deposits that seem harmless) or larger deposits of soft drusen with indistinct borders. Soft drusen accumulating between the retinal pigment epithelium (RPE) and Bruch's membrane force these two structures apart.

Most people over 40 have a small amount of hard drusen, which can join to form soft drusen in AMD cases. However, not all soft drusen come from hard drusen.

There are two types of macular degeneration: the dry or atrophic type, and the wet or hemorrhagic type. The dry form of AMD, which constitutes 80% of all AMD patients, is characterized by the appearance of drusen. The presence of drusen is considered to be a pre-existing factor associated with the progression of the disease to either advanced dry AMD or wet AMD.

Alzheimer's Disease

Alzheimer's disease (AD) is an age-related progressive neurodegenerative disorder characterized by memory loss and severe cognitive decline (Hardy & Selkoe, 2002). The clinical features are manifested morphologically by excessive accumulation of extracellular aggregations of amyloid β-peptide (Aβ) in the form of amyloid plaques in the brain parenchyma, particularly in the hippocampus and cerebral cortex, leading to neuronal loss (Selkoe, 1991). In addition, in most mouse models of Alzheimer's disease the neurogenesis that normally occurs throughout life in the hippocampus of the adult brain is disrupted (Haughey et al., 2002). In Alzheimer patients, like in transgenic mice (PDGF-APPSw, Ind), some increase in neurogenesis takes place but is apparently not sufficient to overcome the disease (Jin et al., 2004a, b).

The Similarity Between AMD and Alzheimer's Disease

AMD and Alzheimer's disease are both chronic neurodegenerative disorders that affect a substantial proportion of elderly persons. Characteristic of these disorders is the irreversible loss of function, for which there is no cure. The degeneration occurring in AMD and Alzheimer's disease may, to some extent, have a common pathogenesis (Klayer et al., 1999). Although the etiology of both AMD and Alzheimer's disease is largely unknown, the pathogeneses of the two diseases show some striking similarities. In AMD, early histopathological manifestations are extracellular drusen deposits and basal laminar deposits (Hageman & Mullins, 1999). These lesions contain lipids, glycoproteins and glycosaminoglycans, which are presumably derived from a degenerating neuroretina (Kliffen et al., 1995). Accumulation of these deposits is associated with loss of photoreceptors and subsequent deterioration of macular function (Holz et al., 1994). As noted above, an early pathologic hallmark in Alzheimer's disease is the presence of extracellular senile plaques (Selkoe, 1991). These plaques are composed of many components, including small peptides generated by proteolytic cleavage of a family of transmembrane polypeptides known as amyloid precursor proteins. Two peptides that are widely regarded as major contributors to the pathology of Alzheimer's disease are known as amyloid-β (Aβ) peptides. Shared components of amyloid deposits and drusen include proteins such as vitronectin, amyloid P, apolipoprotein E, and even the Aβ peptides and amyloid oligomers that are associated with amyloid plaques in Alzheimer's disease (Luibl et al., 2006; Mullins et al., 2000; Yoshida et al., 2005).

The Aβ peptides present in Alzheimer's disease activate microglial cells to produce potentially neurotoxic substances such as reactive oxygen and nitrogen species, proinflammatory cytokines, complement proteins, and other inflammatory mediators that bring about neurodegenerative changes (Akiyama et al., 2000). The inflammatory response that has been associated with Alzheimer's disease often involves CD11b$^+$ activated microglia, representing the innate arm of the immune system in the central nervous system (CNS) (Streit, 2004). CD11b$^+$ microglia were reported to be associated with age-related normal human brain (Streit, 2004), and it is possible that such microglia are the ones that contribute both to age-related cognitive loss and to impaired neurogenesis (Monje et al., 2003). CD11b have also been found in patients with Alzheimer's disease (Akiyama & McGeer, 1990). Moreover, inflammatory mediators are present in amyloid deposits as well as in drusen, suggesting a possible common role for the inflammatory pathway in AMD and Alzheimer's disease (Hageman et al., 2001). A role for local inflammation in drusen biogenesis suggests that it is analogous to the process that occurs in Alzheimer's disease, where accumulation of extracellular plaques and deposits elicits a local chronic inflammatory response that exacerbates the effects of primary pathogenic stimuli (Akiyama et al., 2000).

Microglial Activation in Neurodegeneration

Microglia are bone marrow-derived glial cells, which are present within all layers of the adult human retina (Penfold et al., 1991). Several types are present which may be associated with neurons or with blood vessels, and some of these are antigen-presenting cells (APCs) (Penfold et al., 1991; Provis, 2001). The nature of microglial activation, either beneficial or harmful, in damaged neural tissue depends on how microglia interpret the threat (Butovsky et al., 2005). Although the presence of microglial cells in normal undamaged neural tissue has been debated for years, it is now an accepted fact (Nimmerjahn et al., 2005), including their presence in the eye. The role of microglia in inflammatory processes is controversial. On the one hand, participation of microglia in inflammatory process of the eye can stimulate mature retinal ganglion cells (RGCs) to regenerate their axons (Yin et al., 2003). On the other hand, the role of microglia in neurodegenerative processes may be detrimental to the neuronal tissue. Roque et al (1999) showed that microglial cells release soluble product(s) that induce degeneration of cultured photoreceptor cells. This controversy may be explained by the contradicting reports regarding the presence of antigen-presenting cells, which are crucial factors of an antigen-specific cell-mediated immune response. Immunological responses in neural retinal microglia are related to early pathogenic changes in retinal pigment epithelium pigmentation and drusen formation. Activated microglia may also be involved in rod cell death in AMD and late-onset retinal degeneration. A recent study has proposed that microglia, activated by primary rod cell death, migrate to the outer nuclear layer, remove rod cell debris and may kill adjacent cone photoreceptors (Gupta et al., 2003).

Like blood-derived macrophages, microglia exhibit scavenging of extracellular deposits, and phagocytosis of abnormal amyloid deposits in Alzheimer's disease. Such microglia, while efficiently acting as phagocytic cells, cause neuronal death by the secretion of mediators like tumor necrosis factor alpha (TNF-α) (Butovsky et al., 2005), and thus, while acting as phagocytic cells (Frenkel et al., 2005), they are apparently not efficient enough to fight off the Alzheimer's disease symptoms. In contrast to these resident microglia, microglia derived from the bone marrow of matched wild-type mice can effectively remove plaques (Simard et al., 2006). Moreover, an absence of normally functioning macrophages lead to the development of clinical AMD (Ambati et al., 2003). Thus, AMD, like Alzheimer's disease, illustrates a disease in which scavenging of abnormal deposits inevitably induces self-perpetuation of disease progression mediated by the phagocytic cell themselves (Gupta et al., 2003).

Protective Autoimmunity

Some years ago our group formulated the concept of 'protective autoimmunity' (Moalem et al., 1999). Both pro-inflammatory and anti-inflammatory cytokines were found to be critical components of a T cell-mediated beneficial autoimmune response, provided that the timing and the intensity of the T-cell activity was suitably controlled (Butovsky et al., 2005; Shaked et al., 2004), and depending on the nature of the disease (Schwartz et al., 2006). According to our concept, an uncontrolled autoimmunity leads to the commonly known condition of autoimmune diseases associated with overwhelmed activation of microglia (Butovsky et al., 2006a), as will be discussed below. The beneficial effect of the autoreactive T cells was found to be exerted via their ability to induce the CNS-resident microglia to adopt a phenotype capable of presenting antigens (Butovsky et al., 2001; Butovsky et al., 2005; Schwartz et al., 2006; Butovsky et al., 2006a; Shaked et al., 2004), expressing growth factors (Butovsky et al., 2005; Butovsky et al., 2006a;b), and buffering glutamate (Shaked et al., 2005).

In attempting to boost the efficacy of the protective autoreactive T cells, we tested many compounds in the search for a safe and suitable antigen for neuroprotection. We then suggested to use glatiramer acetate, also known as Copolymer 1 or Cop-1 (Kipnis et al., 2000; Avidan et al., 2004; Angelov et al., 2003), a synthetic 4-amino-acid copolymer known to be safe and currently used as a treatment for multiple sclerosis by a daily administration regimen (Copaxone®, Teva Pharmaceutical Industries Ltd., Israel). In our studies we have demonstrated its low-affinity cross-reaction with a wide range of CNS autoantigens. Because the affinity of cross-reaction is low, the Cop-1-activated T cells, after infiltrating the CNS, have the potential to become locally activated with little or no attendant risk of autoimmune disease (Kipnis et al., 2000).

A single injection of Cop-1 is protective in acute models of CNS insults (Kipnis et al., 2000; Avidan et al., 2004; Kipnis & Schwartz, 2002), while in chronic models occasional boosting is required for a long-lasting protective effect (Angelov et al., 2003). In the rat model of chronically high intraocular pressure, vaccination with Cop-1 significantly reduces RGC loss even if the pressure remains high. It should be noted that the vaccination does not prevent disease onset, but can slow down its progression by controlling the local extracellular environment of the nerve and retina, making it less hostile to neuronal survival and allowing the RGCs to be better able to withstand the stress (Schori et al., 2001; Benner et al., 2004; Kipnis & Schwartz, 2002; Kipnis et al., 2000).

For chronic conditions occasional boosting is needed. For example, in a model of chronically elevated intraocular pressure, weekly administration of adjuvant-free Cop-1 was found to result in neuroprotection (Bakalash et al., 2005). The neuroprotective effect of Cop-1 has been attributed in part to production of brain-derived neurotrophic factor (BDNF) (Kipnis et al., 2004b; Ziemssen et al., 2002).

Aggregated Aβ Induces Toxicity on Resident Microglia and Impairs Cell Renewal

Recent studies performed in our laboratory suggested that microglia exposed to aggregated Aβ, although effective in removing plaques, are toxic to neurons and impair neural cell renewal (Butovsky et al., 2006a); these effects are reminiscent of the response of microglia to invading microorganisms (as exemplified by their response to LPS) (Butovsky et al., 2005; Schwartz et al., 2006). Such activities are manifested by increased production of TNF-α, down-regulation of insulin-like growth factor (IGF-I), inhibition of the ability to express class II major histocompatibility complex (MHC-II) proteins and CD11c (a marker of dendritic cells) and thus to act as antigen-presenting cells (APCs), and failure to support neural tissue survival and renewal ((Butovsky et al., 2006a; Butovsky et al., 2005; Butovsky et al., 2006b). Further, we found that when microglia encounter aggregated β-amyloid, their ability to remove these aggregates without exerting toxic effects on neighboring neurons or impairing neurogenesis depends upon their undergoing a phenotype switch. A switch in microglial phenotype might take place via a local dialog between microglia and T-cells, which is mediated by T cell-derived cytokines such as interleukin (IL)-4. Addition of IL-4, a cytokine derived from T-helper (Th)-2 cells, to microglia activated by aggregated Aβ can reverse the down-regulation of IGF-I expression, the up-regulation of TNF-α expression, and the failure to act as APCs (Butovsky et al., 2005). The significance of microglia for in-vivo neural cell renewal was demonstrated by enhanced neurogenesis in the rat dentate gyrus after injection of IL-4-activated microglia intracerebroventricularly and by the presence of IGF-1-expressing microglia in the dentate gyms of rats kept in an enriched environment (Ziv et al., 2006). In rodents with acute or chronic EAE, injection of IL-4-activated microglia into the cerebrospinal fluid resulted in increased oligodendrogenesis in the spinal cord and improved clinical symptoms. The newly formed oligodendrocytes were spatially associated with microglia expressing MHC-II and IGF-I (Butovsky et al., 2006c).

In Both Alzheimer's Disease and AMD there are Systemic Components

Our first observation that systemic immune cells (in the form of T cells directed to certain self-antigens) can protect injured neurons from death came from studies in rodents showing that passive transfer of T cells specific to myelin basic protein reduces the loss of RGCs after a traumatic optic nerve injury (Moalem et al., 1999). We found that these T cells are also effective when directed to either cryptic or pathogenic epitopes of myelin basic protein, as well as to other myelin antigens or their epitopes (Mizrahi et al., 2002). These findings raised a number of critical questions. For example, are myelin antigens capable of protecting the nervous system from any type of acute or chronic insult? Is the observed neuroprotective activity of immune cells merely an anecdotal finding reflecting our experimental conditions, or does it point to the critical participation of the immune system in fighting off injurious conditions in the visual system and in the CNS in general? If the latter, does it mean that neurodegenerative diseases are systemic diseases? If so, can this finding be translated into a systemic therapy that would protect the brain, the eye, and the spinal cord?

In a series of experiments carried out over the last few years we have learned, firstly, that protective T cell response is a physiologically evoked response that might not be sufficient in severe insults or might not always be properly controlled. Moreover, we discovered that the specificity of such protective T cells depends on the site of the insult. Thus, for example, the protective effect of vaccination with myelin-associated antigens is restricted to injuries of the white matter, i.e., to myelinated axons (Mizrahi et al., 2002; Avidan et al., 2004; Schori et al., 2001). If the insult is to the retina, which contains no myelin, myelin antigens have no effect. Secondly, we observed that the injury-induced response of T cells reactive to specific self-antigens residing in the site of stress (eye or brain) is a spontaneous physiological response (Yoles et al., 2001). We then sought to identify the phenotype of the beneficial autoimmune T cells and to understand what determines the balance between a beneficial (neuroprotective) outcome of the T cell-mediated response to a CNS injury and a destructive effect causing autoimmune disease. We also examined ways of translating the beneficial response into a therapy for glaucoma. We found that in immune deficient animals the number of surviving RGCs following an insult in the eye, the spinal cord or the brain is significantly lower than in matched controls with an intact immune system, suggesting that the ability to withstand insult to the CNS depends on the integrity of the immune system and specifically on specific population within the immune system; those that recognize the site-specific self-antigens. Interestingly, the use of steroids caused significant loss of RGCs (Bakalash et al., 2003).

T Cells Specific to Antigens Residing in the Site of Damage Help Clean and Heal

In order to be protective, the anti-self T cells should home to the site of damage and be locally activated. This is why only those antigens that are being presented at the site of lesion can be used for the vaccination. Once activated, the T cells provide a source of cytokines and growth factors that shape the resident eye sentinels cells—the microglia, so as to make them active defensible cells that the eye can tolerate. Namely, such activated microglia can take up glutamate, remove debris and produce growth factors while refraining from production of agents that are part of their killing mechanism (e.g. TNF-α) to which the eye, like the brain, has a low tolerance (Butovsky et al., 2005; Butovsky et al., 2001; Barouch & Schwartz, 2002; Moalem et al., 2000; Shaked et al., 2005).

Such T cells are constitutively controlled by physiologically existing regulatory T cells that are themselves amenable to control upon need (Kipnis et al., 2004a; Kipnis et al., 2002).

Reference is made to copending International Patent Application No. PCT/IL2007/000797 entitled "Activated myeloid cells for promoting tissue repair and detecting damaged tissue" filed by applicant at the Israel PCT Receiving Office (RO/IL) on the same date, the contents thereof being explicitly excluded from the scope of the present invention.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to provide an immune-based therapy for age-related macular degeneration.

In one aspect, the present invention relates to a method for treatment of age-related macular degeneration, which comprises causing T cells that produce IL-4 to accumulate in the eye of a patient in need, thereby halting or delaying progress of the macular degeneration.

In one embodiment, the accumulation of T cells in the eye is caused by administering to said patient an agent selected from the group consisting of:
 (i) Copolymer-1, a Copolymer-1-related-peptide, or a Copolymer 1-related polypeptide;
 (ii) IL-4;
 (iii) dendritic cells, monocytes, bone marrow-derived myeloid cells or peripheral blood mononuclear cells activated by IL-4;
 (iv) genetically engineered cells that produce IL-4;
 (v) bone marrow-derived myeloid cells or peripheral blood-derived myeloid cells activated with IL-13 or with up to 20 ng/ml IFN-γ;
 (vi) a pathogenic self-antigen associated with a T-cell-mediated specific autoimmune disease of the eye;
 (vii) a peptide which sequence is comprised within the sequence of said pathogenic self-antigen of (vi) or a peptide obtained by modification of said peptide, which modification consists in the replacement of one or more amino acid residues of the peptide by different amino acid residues (hereinafter "modified peptide"), said modified peptide still being capable of recognizing the T-cell receptor recognized by the parent peptide but with less affinity;
 (viii) a nucleotide sequence encoding a pathogenic self-antigen of (vi) or a peptide or a modified peptide of (vii);
 (ix) T cells activated by an agent of (i), (vi) or (vii); and
 (x) any combination of (i)-(ix).

In another aspect, the invention relates to the use of an agent as defined in (i)-(x) above for the preparation of a medicament for treatment of age-related macular degeneration.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1A) In-vitro treatment paradigm. (FIG. 1B) Representative confocal microscopic images of neural progenitor cells (NPCs) expressing green fluorescent protein (GFP) and βIII-T (neuronal marker), co-cultured for 10 days without microglia (MG, control), or with untreated microglia, or with microglia that were pre-activated by aggregated $Aβ_{(1-40)}$ (5 μM) ($MG_{(Aβ1-40)}$) for 48 h and subsequently activated with IFN-γ (10 ng/ml) ($MG_{(Aβ1-40/IFNγ)}$) or with IL-4 (10 ng/ml) ($MG_{(Aβ1-40/IL-4)}$) or with both IFN-γ (10 ng/ml) and IL-4 (10 ng/ml) ($MG_{(Aβ1-40/IFNγ+IL-4)}$). Note, aggregated Aβ induced microglia to adopt an amoeboid morphology, but after IL-4 was added they exhibited a ramified structure. (FIG. 1C) Separate confocal images of NPCs co-expressing GFP and βIII-T adjacent to $CD11b^+$ microglia. (FIG. 1D) Quantification of cells double-labeled with GFP and βIII-T (expressed as a percentage of $GFP^+$ cells) obtained from confocal images. Results are of three independent experiments in replicate cultures; bars represent means±SEM. Asterisks above bars denote the significance of differences relative to untreated (control) NPCs (*$P<0.05$; ***$P<0.001$; two-tailed Student's t-test). Horizontal lines with P values above them show differences between the indicated groups (ANOVA).

(FIG. 2A) Representative confocal microscopic images of brain hippocampal slices from non-transgenice (Tg), untreated-Tg-Alzheimer's disease (AD), and Cop-1-vaccinated Tg-AD mice stained for NeuN (mature neurons) and human Aβ. The non-Tg mouse shows no staining for human Aβ. The untreated-Tg-AD mouse shows an abundance of extracellular Ali plaques, whereas in the Cop-1-treated Tg-AD mouse Aβ-immunoreactivity is low. Weak $NeuN^+$ staining is seen in the hippocampal CA1 and dentate gyrus regions of the untreated-Tg-AD mouse relative to its non-Tg littermate, whereas $NeuN^+$ staining in the Cop-1-vaccinated Tg-AD mouse is almost normal. (FIG. 2B) Staining for activated microglia using anti-CD11b antibodies. Images at low and high magnification show a high incidence of microglia double-stained for Aβ and CD11b in the CA1 and dentate gyrus regions of the hippocampus of an untreated-Tg-AD mouse, but only a minor presence of $CD11b^+$ microglia in the Cop-1-vaccinated Tg-AD mouse. Arrows indicate areas of high magnification, shown below. (FIG. 2C) $CD11b^+$ microglia, associated with an Aβ plaque, strongly expressing TNF-α in an untreated-Tg-AD mouse. (FIG. 2D) Staining for MHC-II (a marker of antigen presentation) in a cryosection taken from a Cop-1-vaccinated Tg-AD mouse in an area that stained positively for Aβ shows a high incidence of $MHC-II^+$ microglia and almost no $TNF-α^+$ microglia. (FIG. 2E) All $MHC-II^+$ microglia in a brain area that stained positively for Aβ (arrowheads) in a Cop-1-vaccinated Tg-AD mouse co-express CD11c (a marker of dendritic cells), but only a few $CD11c^+/MHC-II^+$ microglia are seen in a corresponding area in the brain of an untreated-Tg-AD mouse. (FIG. 2F) $MHC-II^+$ microglia in a Cop-1-vaccinated Tg-AD mouse co-expresses IGF-I. (FIG. 2G) $CD3^+$ T cells are seen in close proximity to an Aβ-plaque and (FIG. 2H) are associated with $MHC-II^+$ microglia. Boxed area shows high magnification of an immunological synapse between a T cell ($CD3^+$) and a microglial cell expressing MHC-II. (FIG. 2I) Histogram showing the total number of Aβ-plaques (in a 30-μm hippocampal slice). (FIG. 2J) Histogram showing staining for Aβ-immunoreactivity. Note the significant differences between Cop-1-vaccinated Tg-AD and untreated-Tg-AD mice, verifying the decreased presence of Aβ-plaques in the vaccinated mice. (FIG. 2K) Histogram showing a marked reduction in cells stained for CD11b, indicative of activated microglia and inflammation, in the Cop-1-vaccinated Tg-AD mice relative to untreated-Tg-AD mice. Note the increase in CD1 microglia with age in the non-Tg littermates. (FIG. 2L) Histogram showing significantly more $CD3^+$ cells associated with an Aβ-plaque in Cop-1-vaccinated Tg-AD mice than in untreated-Tg-AD mice. Quantification of $CD3^+$ cells was analyzed from 30-50 plaques of each mouse tested in this study. Error bars indicate means±SEM. *$P<0.05$, ***$P<0.001$ versus non-Tg littermates (Student's t-test). The P values indicated in the figure represent a comparison of the groups as analyzed by ANOVA. All of the mice in this study were included in the analysis (6-8 sections per mouse).

FIGS. 3A-3C show that Cop-1 vaccination induces microglia to express CD11c. (FIG. 3A) $CD11b^+$ microglia co-expressing CD11c surround an Aβ-plaque in Cop-1-vaccinated Tg-AD mice. All of the CD11c-expressing microglia are co-labeled for CD11b. Separate confocal channel is shown in right panel. (FIG. 3B) Histograms showing the number of $CD11b^+$ cells associated with Aβ-plaque. (FIG. 3C) Histograms showing quantification of $CD11c^+$ cells as a percentage of the total number of $CD11b^+$ and $CD11c^+$ cells associated with an Aβ-plaque. For this analysis, cells were counted surrounding 30-50 plaques in each mouse tested. Error bars represent means±SEM. Asterisks above bars denote the significance of differences between the groups ($P<0.01$; *$P<0.001$; two-tailed Student's t-test).

(FIG. 4A) IL-4-activated microglia ($MG_{(IL-4)}$) induce CD11c expression in a primary culture of mouse microglia 5 days after activation. Untreated microglia ($MG_{(Aβ)}$) express hardly any CD11c. (FIG. 4B) Effect of IL-4 (in terms of morphology and CD11c expression) on microglia pretreated for 3 days with aggregated $Aβ_{(1-40)}$ ($MG_{(Aβ)}$) and assessed 10 days later compared to IL-4 treatment for 10 days without pre-exposure to Aβ. Note that dendritic-like morphology was adopted upon addition of IL-4 to the Aβ-pretreated microglia only, whereas CD11c expression was induced by IL-4 both with and without Aβ pretreatment. (FIG. 4C) Quantitative analysis of microglial expression of $CD11c^+$ microglia (expressed as a percentage of IB-4-labeled microglia) and of CD11c intensity per cell, both expressed as a function of time in culture with or without IL-4. (FIG. 4D) Quantitative analysis of CD11c expression (calculated as a percentage of IB-4-labeled microglia) by the cultures shown in (FIG. 4B). Results are of three independent experiments in replicate cultures; bars represent means±SEM. Asterisks above bars denote the significance of differences relative to untreated microglia at each time point (***$P<0.001$; two-tailed Student's t-test).

(FIG. 5A) Confocal photomicrographs. (FIG. 5B) Quantitative analysis expressed as intensity per cell. Results of one of two experiments, each containing eight replicates (20-30 cells per replicate) per group are presented (means±SD).

(FIGS. 6A-6C) Histograms showing quantification of the proliferating cells (BrdU$^+$). (FIG. 6A) Newly formed mature neurons (BrdU$^+$/NeuN$^+$) (FIG. 6B), and all pre-mature (DCX$^+$-stained) neurons (FIG. 6C). Numbers of BrdU$^+$, BrdU$^+$/NeuN$^+$ and DCX$^+$ cells per dentate gyrus (DG), calculated from six equally spaced coronal sections (30 μm) from both sides of the brains of all the mice tested in this study. Error bars represent means±SEM. Asterisks above bars denote the significance of differences relative to non-Tg littermates ($P<0.01$; *$P<0.001$; two-tailed Student's t-test). Horizontal lines with P values above them show differences between the indicated groups (ANOVA). (FIG. 6D) Representative confocal microscopic images of the dentate gyrus showing immunostaining for BrdU/DCX/NeuN in a Cop-1-vaccinated Tg-AD mouse and in a non-Tg littermate relative to that in an untreated-Tg-AD mouse. (FIG. 6E) Branched DCX$^+$ cells are found near MHC-II$^+$ microglia located in the subgranular zone (SGZ) of the hippocampal dentate gyrus of a Cop-1-vaccinated Tg-AD mouse.

(FIGS. 7A-7B) Cop-1-vaccinated Tg-AD mice (diamond; n=6) showed significantly better learning/memory ability than untreated-Tg-AD mice (square; n=7) during the acquisition and reversal. Untreated-Tg-AD mice showed consistent and long-lasting impairments in spatial memory tasks. In contrast, performance of the MWM test by the Cop-1-vaccinated Tg-AD mice was rather similar, on average, to that of their age-matched naïve non-Tg littermates (triangle; n=6) (3-way ANOVA, repeated measures: groups, df (2.16), F=22.3, P<0.0002; trials, df (3.48), F=67.9, P<0.0001; days, df (3.48), F=3.1, P<0.035, for the acquisition phase; and groups, df (2.16), F=14.9, P<0.0003; trials, df (3.48), F=21.7, P<0.0001; days, df (1.16), F=16.9, P<0.0008, for the reversal phase).

(FIG. 8A) Microglia were treated with IFN-γ (10 ng/ml; MG$_{(IFN-\gamma)}$) or IL-4 (10 ng/ml; MG$_{(IL-4)}$) for 1, 3, 5, 10 and 18 days. Untreated microglia (MG$_{(-)}$) were used as controls. (FIG. 8B) Confocal images of microglia, identified by staining for IL-4, immunolabeled for βIII-T and CD11c after 5 days of treatment. MG$_{(-)}$ did not express CD11c. After exposure to IFN-γ or IL-4 the microglia expressed CD11c and exhibited their characteristic morphology. (FIG. 8C) Co-expression of and CD11c in microglia activated with IFN-γ (10 ng/ml) for 5 days (IL-4/βIII-T/CD11c). Note, confocal channels are presented separately. (FIG. 8D) Quantitative analysis of the numbers of CD11c$^+$ microglia (expressed as a percentage of IL-4$^+$ (microglia marker) cells) were examined in all treatments at all time points. Results are of four independent experiments with duplicate or triplicate wells; bars represent means±SEM. Asterisks above bars denote the significance of differences relative to MG$_{(-)}$ (*$P<0.05$; $P<0.01$; *$P<0.001$; two-tailed Student's t-test). Horizontal lines with P values above them show differences between the indicated groups (ANOVA).

DETAILED DESCRIPTION OF THE INVENTION

Figure 1A:
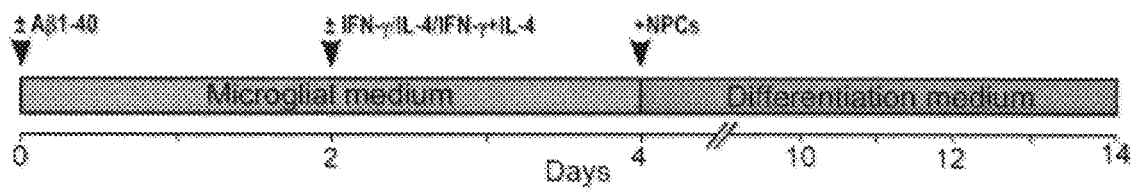
FIGS. 1A-1D demonstrate that IL-4 can counteract the adverse effect of aggregated Aβ on microglial toxicity and promotion of neurogenesis in adult mouse neural progenitor cells.

In searching for a prospect for a T-cell-based vaccination for treatment of AMD, the following considerations may be relevant.

In general, the brain, like the retina, is considered to be immune privileged in the sense that the blood-brain barrier resists passive deposition of antibodies and reduces the recruitment of antigen-specific lymphocytes (Streilein et al., 1992). Paradoxically, antigen-specific immunity might actually function to protect against degenerative diseases. Recently, it was shown in a Alzheimer's disease mouse model that immunization with the abnormal amyloid, or passive administration of antibodies against the abnormal protein, greatly reduced the quantity of deposition in the brain of the genetically modified mice, and improved their performance in laboratory tests of memory and cognitive function (e.g. Morgan et al., 2000). The mechanisms are unclear, but may be related to enhanced phagocytosis, neutralization of toxic molecules, or interference with amyloid fibril aggregation. In Alzheimer's disease however, patients may be immunologically tolerant to amyloid, preventing protective autoimmunization to the abnormally processed protein and thus developing autoimmune encephalomyelitis (Furlan et al., 2003).

Studies from our the laboratory over the last few years have shown that recovery from CNS injury is critically dependent on, the well-controlled activity of T cells directed to specific CNS autoantigens (Moalem et al., 1999; Yoles et al., 2001; Kipnis et al., 2002). After homing to the site of damage, these autoreactive T cells evidently regulate microglia in a way that renders them supportive of neuronal survival and neural tissue repair (Butovsky et al., 2005; Schwartz et al., 2006; Butovsky et al., 2001; Shaked et al., 2005).

Our results herein argue in favor of the use of a myelin-related antigen such as Cop-1, but not an Aβ peptide, as a T cell-based therapy for AMD. Even if any T cells expressing T-cell receptors for drusen-associated peptides such as Aβ were to home to the site of a CNS lesion (Monsonego et al., 2006), it is unlikely that they would encounter their relevant APCs there, and they would therefore not be able to become locally activated.

On the other hand, myelin-presenting microglia, with which myelin-specific T cells can readily hold a dialog, are likely to be present at the damaged sites. Myelin-related antigens, or antigens that are weakly cross-reactive with myelin (such as Cop-1), are therefore likely to be the antigens of choice for therapeutic vaccination (Avidan et al., 2004). T cells activated by these antigens will then home to the CNS and, upon encountering their relevant APCs there, become locally activated to supply the cytokines and growth factors in order to switch the phenotype of the harmful microglia (activated by aggregated Aβ; Butovsky et al., 2005) into microglia with dendritic-like characteristics. The resulting immunological synapse between T cells and microglia will then create a supportive niche for cell renewal by promoting neurogenesis from the pool of adult stem cells (Butovsky et al., 2006a).

Our results indicate that T cells constitute the immune-based therapy of choice for AMD. This does not preclude the potential benefit of antibodies as a supplementary therapy as shown in anima; model of Alzheimer disease with antibodies against Aβ peptide (Bard et al., 2000). Moreover, the T cells can function as a mini-factory capable of producing a variety of compounds, including cytokines and neurotrophic factors (Ziemssen et al., 2002). Above all, they represent a physiological system of maintenance and repair that might help to counteract the age-related conditions leading to brain senescence.

In developing the immune-based therapy for AMD according to the present invention we thus took into consideration the lessons from neurodegenerative diseases with similar pathogenicity.

Formation of extracellular deposits consisting of misfolded protein is the hallmark of many neurodegenerative diseases. The accumulation of amyloid in drusen and Alzheimer's disease and the presence of activated microglia as inflammatory mediators in both neurodegenerative conditions, suggests a possible common chronic inflammatory pathway in AMD and Alzheimer's disease. In the context of Alzheimer's disease we have recently demonstrated that aggregated β-amyloid (Aβ) activates microglia to acquire a phenotype which is reminiscence of that activated by microorganisms. Although such microglia/macrophage can act as phagocytic cells their overall activity is cytotoxic and can hardly be tolerated by the brain. As a result, microglia activated by Aβ rather than help the suffering tissue further contribute to the chaos. In the present invention, we explore possible immune-based therapy to modulate microglia activity in Alzheimer's disease and AMD with the target of maintaining their phagocytic activity while conferring their ability to support cell survival and renewal.

As shown herein, aggregated Aβ induces microglia to become cytotoxic and block neurogenesis from adult rodent neural progenitor cells (NPCs). Addition of IL-4, a cytokine derived from T-helper (Th)$_2$ cells, to microglia activated by Aβ can reverse the impediment, the down-regulation of IGF-I, the up-regulation of TNF-α, and the failure to act as APCs. Using Alzheimer's disease double-transgenic mice expressing mutant human genes encoding presenilin 1 and chimeric mouse/human amyloid precursor protein, we show that switching of microglia phenotype into professional APCs producing IGF-I, achieved here by a T cell-based vaccination with Copolymer-1, resulted in reduction of amyloid loads and the induction of neuronal survival and neurogenesis.

The present invention thus relates to a method for treatment of age-related macular degeneration (AMD), which comprises causing T cells that produce IL-4 to accumulate in the eye of an individual in need, thereby halting or delaying progress of the macular degeneration. This effect can be affected by several self antigens and cytokine activated cells.

In one embodiment, the agents that can cause T cells producing IL-4 to accumulate in the eye include, without being limited to:

(i) Copolymer-1, a Copolymer-1-related-peptide, or a Copolymer 1-related polypeptide;
(ii) IL-4;
(iii) dendritic cells, monocytes, bone marrow-derived myeloid cells or peripheral blood mononuclear cells activated by IL-4;
(iv) genetically engineered cells that produce IL-4;
(v) bone marrow-derived myeloid cells or peripheral blood-derived myeloid cells activated with IL-13 or with up to 20 ng/ml IFN-γ;
(vi) a pathogenic self-antigen associated with a T-cell-mediated specific autoimmune disease of the eye;
(vii) a peptide which sequence is comprised within the sequence of said pathogenic self-antigen of (vi) or a peptide obtained by modification of said peptide, which modification consists in the replacement of one or more amino acid residues of the peptide by different amino acid residues (hereinafter "modified peptide"), said modified peptide still being capable of recognizing the T-cell receptor recognized by the parent peptide but with less affinity;
(viii) a nucleotide sequence encoding a pathogenic self-antigen of (vi) or a peptide or a modified peptide of (vii);
(ix) T cells activated by an agent of (i), (vi) or (vii); and
(x) any combination of (i)-(ix).

In one preferred embodiment, the agent is Copolymer 1, a Copolymer 1-related peptide or a Copolymer 1-related polypeptide.

For the purpose of the present invention, "Copolymer 1 or a Copolymer 1-related peptide or polypeptide" is intended to include any peptide or polypeptide, including a random copolymer that cross-reacts functionally with MBP and is able to compete with MBP on the MHC class II in the antigen presentation.

The Cop 1 or a Cop 1-related peptide or polypeptide is represented by a random copolymer consisting of a suitable ratio of a positively charged amino acid such as lysine or arginine, in combination with a negatively charged amino acid (preferably in a lesser quantity) such as glutamic acid or aspartic acid, optionally in combination with a non-charged neutral amino acid such as alanine or glycine, serving as a filler, and optionally with an amino acid adapted to confer on the copolymer immunogenic properties, such as an aromatic amino acid like tyrosine or tryptophan. Such copolymers are disclosed, for example, in WO 00/05250, the entire contents of which are herewith incorporated herein by reference.

More specifically, the Copolymer 1 or a Copolymer 1-related peptide or polypeptide is a copolymer selected from the group consisting of random copolymers comprising one amino acid selected from each of at least three of the following groups: (a) lysine and arginine; (b) glutamic acid and aspartic acid; (c) alanine and glycine; and (d) tyrosine and tryptophan. The amino acids may be L- or D-amino acids or mixtures thereof. The present invention contemplates the use of copolymers containing both D- and L-amino acids, as well as copolymers consisting essentially of either L- or D-amino acids.

In one embodiment of the invention, the copolymer contains four different amino acids, each from a different one of the groups (a) to (d).

In a more preferred embodiment, the agent is Copolymer 1, composed of a mixture of random polypeptides consisting essentially of the amino acids L-glutamic acid (E), L-alanine (A), L-tyrosine (Y) and L-lysine (K) in an approximate ratio of 1.5:4.8:1:3.6, having a net overall positive electrical charge and of a molecular weight from about 2 KDa to about 40 KDa.

In one preferred embodiment, the Cop 1 has average molecular weight of about 2 KDa to about 20 KDa, more preferably of about 4.7 KDa to about 13 K Da, still more preferably of about 4 KDa to about 8.6 KDa, of about 5 KDa to 9 KDa, or of about 6.25 KDa to 8.4 KDa. In another preferred embodiment, the Cop 1 has average molecular weight of about 13 KDa to about 20 KDa, more preferably of about 13.5 KDa to about 18 KDa, with an average of about 15 KDa to about 16 KD, preferably of 16 kDa. Other average molecular weights for Cop 1, lower than 40 KDa, are also encompassed by the present invention. Copolymer 1 of said molecular weight ranges can be prepared by methods known in the art, for example by the processes described in U.S. Pat. No. 5,800,808, the entire contents of which are hereby incorporated by reference in the entirety. The Copolymer 1 may be a polypeptide comprising from about 15 to about 100, preferably from about 40 to about 80, amino acids in length.

In one more preferred embodiment of the invention, the agent is Cop 1 in the form of its acetate salt known under the generic name glatiramer acetate or its trade name Copaxone® (a trademark of Teva Pharmaceutical Industries Ltd., Petach Tikva, Israel). As used herein in the application, the terms "Cop 1", "Copolymer 1", "glatiramer acetate" and "GA" are used interchangeably.

In another embodiment, the Copolymer 1-related peptide is a random copolymer of 4 amino acids in which one or more of the following substitutions is made: aspartic acid for glutamic acid, glycine for alanine, arginine for lysine, and tryptophan for tyrosine, which is expected to have the same activity of Copolymer.

In another embodiment of the invention, the Cop 1-related peptide or polypeptide is a copolymer of three different amino acids each from a different one of three groups of the groups (a) to (d). These copolymers are herein referred to as terpolymers. In one embodiment, the terpolymer contains tyrosine (Y), alanine (A), and lysine (K), hereinafter designated YAK, in which the average molar fraction of the amino acids can vary: Y, A and K can be present in a mole fraction of about 0.05-0.250, 0.3-0.6; and 0.1-0.5, respectively, more preferably, the molar ratios of Y, A and K are about 0.10:0.54:0.35, respectively. It is possible to substitute arginine for lysine, glycine for alanine, and/or tryptophan for tyrosine.

In another embodiment, the terpolymer contains tyrosine (Y), glutamic acid (E), and lysine (K), hereinafter designated YEK, in which the average molar fraction of the amino acids can vary: E, Y and K can be present in a mole fraction of about 0.005-0.300, 0.005-0.250, and 0.3-0.7, respectively. More preferably, the molar ratios of E, Y and K are about 0.26:0.16:0.58, respectively. It is possible to substitute aspartic acid for glutamic acid, arginine for lysine, and/or tryptophan for tyrosine.

In another embodiment, the terpolymer contains lysine (K), glutamic acid (E), and alanine (A), hereinafter designated KEA, in which the average molar fraction of the amino acids can vary: E, A and K van be present in a mole fraction of about 0.005-0.300, 0.005-0.600, and 0.2-0.7, respectively. More preferably, the molar ratios of E, A and K are about 0.15:0.48:0.36, respectively. It is possible to substitute aspartic acid for glutamic acid, glycine for alanine, and/or arginine for lysine.

In a further embodiment, the terpolymer contains tyrosine (Y), glutamic acid (E), and alanine (A0, hereinafter designated YEA, in which the average molar fraction of the amino acids can vary: Y, E and A can be present in a mole fraction of about 0.005-0.250, 0.005-0.300, and 0.005-0.800, respectively. More preferably, the molar ratios of E, A, and Y are about 0.21:0.65:0.14, respectively. It is possible to substitute tryptophan for tyrosine, aspartic acid for glutamic acid, and/or glycine for alanine.

The average molecular weight of the terpolymers YAK, YEK, KEA and YEA can vary between about 2 KDa to 40 KDa, preferably between about 3 KDa to 35 KDa, more preferably between about 5 KDa to 25 KDa.

Copolymer 1 and related peptides and polypeptides may be prepared by methods known in the art, for example, by the process disclosed in U.S. Pat. No. 3,849,550. The molecular weight of the copolymers can be adjusted during polypeptide synthesis or after the copolymers have been made. To adjust the molecular weight during polypeptide synthesis, the synthetic conditions or the amounts of amino acids are adjusted so that synthesis stops when the polypeptide reaches the approximate length that is desired. After synthesis, polypeptides with the desired molecular weight can be obtained by any available size selection procedure, such as chromatography of the polypeptides on a molecular weight sizing column or gel, and collection of the molecular weight ranges desired. The copolymers can also be partially hydrolyzed to remove high molecular weight species, for example, by acid or enzymatic hydrolysis, and then purified to remove the acid or enzymes.

In one embodiment, the copolymers with a desired molecular weight may be prepared by a process, which includes reacting a protected polypeptide with hydrobromic acid to form a trifluoroacetyl-polypeptide having the desired molecular weight profile. The reaction is performed for a time and at a temperature that is predetermined by one or more test reactions. During the test reaction, the time and temperature are varied and the molecular weight range of a given batch of test polypeptides is determined. The test conditions that provide the optimal molecular weight range for that batch of polypeptides are used for the batch. Thus, a trifluoroacetyl-polypeptide having the desired molecular weight profile can be produced by a process, which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight. In one embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

As binding motifs of Cop 1 to MS-associated HLA-DR molecules are known (Fridkis-Hareli et al, 1999), polypeptides derived from Cop 1 having a defined sequence can readily be prepared and tested for binding to the peptide binding groove of the HLA-DR molecules as described in the Fridkis-Hareli et al (1999) publication. Examples of such peptides are those disclosed in WO 00/05249 and WO 00/05250, the entire contents of which are hereby incorporated herein by reference, and include the peptides of SEQ ID NOs. 1-32 hereinbelow.

```
AAAYAAAAAKAAAA        SEQ ID NO: 1
AEKYAAAAAAKAAAA       SEQ ID NO: 2
AKEYAAAAAAKAAAA       SEQ ID NO: 3
AKKYAAAAAAKAAAA       SEQ ID NO: 4
AEAYAAAAAAKAAAA       SEQ ID NO: 5
KEAYAAAAAAKAAAA       SEQ ID NO: 6
AEEYAAAAAAKAAAA       SEQ ID NO: 7
AAEYAAAAAAKAAAA       SEQ ID NO: 8
EKAYAAAAAAKAAAA       SEQ ID NO: 9
AAKYEAAAAAKAAAA       SEQ ID NO: 10
AAKYAEAAAAKAAAA       SEQ ID NO: 11
EAAYAAAAAAKAAAA       SEQ ID NO: 12
EKKYAAAAAAKAAAA       SEQ ID NO: 13
EAKYAAAAAAKAAAA       SEQ ID NO: 14
AEKYAAAAAAAAAA        SEQ ID NO: 15
AKEYAAAAAAAAAA        SEQ ID NO: 16
AKKYEAAAAAAAAA        SEQ ID NO: 17
AKKYAEAAAAAAAA        SEQ ID NO: 18
AKAYKAAAAAAAAA        SEQ ID NO: 19
KEAYAAAAAAAAAA        SEQ ID NO: 20
```

```
AEEYKAAAAAAAAAA              SEQ ID NO: 21

AAEYKAAAAAAAAAA              SEQ ID NO: 22

EKAYAAAAAAAAAA               SEQ ID NO: 23

AAKYEAAAAAAAAAA              SEQ ID NO: 24

AAKYAEAAAAAAAAA              SEQ ID NO: 25

EKKYAAAAAAAAAA               SEQ ID NO: 26

EAKYAAAAAAAAAA               SEQ ID NO: 27

AEYAKAAAAAAAAA               SEQ ID NO: 28

AEKAYAAAAAAAAA               SEQ ID NO: 29

EKYAAAAAAAAAAA               SEQ ID NO: 30

AYKAEAAAAAAAAA               SEQ ID NO: 31

AKYAEAAAAAAAAA               SEQ ID NO: 32
```

Such peptides of SEQ ID Nos: 1-32 and other similar peptides derived from Cop 1 would be expected to have similar activity as Cop 1. Such peptides, and other similar peptides, are also considered to be within the definition of Cop 1-related peptides or polypeptides and their use is encompassed by the present invention as well as other synthetic amino acid copolymers such as the random four-amino acid copolymers described by Fridkis-Hareli et al., 2002 (as candidates for treatment of multiple sclerosis), namely copolymers (14-, 35- and 50-mers) containing the amino acids phenylalanine, glutamic acid, alanine and lysine (poly FEAK), or tyrosine, phenylalanine, alanine and lysine (poly YFAK), and any other similar copolymer to be discovered that can be considered a universal antigen similar to Cop 1.

In another preferred embodiment of the present invention, the agent that causes T cells that produce IL-4 to accumulate in the eye is IL-4, preferably human recombinant IL-4, that can be administered nasally.

In a further embodiment, the agent is IL-4 activated dendritic cells, IL-4 activated monocytes, IL-4 activated bone marrow-derived myeloid cells or IL-4 activated peripheral blood mononuclear cells (PBMCs). In this regard, IL-13 have the same effect as IL-4, because it is well established in the field of cytokines that IL-4 and IL-13 can utilize a common receptor and share many actions such as B-cell activation and suppression of Th-1 cells.

In an additional embodiment, the agent is bone marrow-derived myeloid cells or peripheral blood-derived myeloid cells activated with IL-13 or with a narrow concentration range of IFN-γ, more preferably up to 20 ng/ml IFN-γ.

In another embodiment, the agent is a mammalian pathogenic self-antigen associated with a T-cell-mediated specific autoimmune disease of the eye such as, but not limited to, a pathogenic uveitogenic antigen selected from mammalian interphotoreceptor retinoid-binding protein (IRBP), S-antigen (S-Ag), or rhodopsin. The mammalian uveitogenic antigen is preferably a human IRBP (SEQ ID NO: 33) or a bovine IRBP (SEQ ID NO: 34), a human S-Ag (SEQ ID NO: 35) or a bovine S-Ag (SEQ ID NO: 36), or human rhodopsin (SEQ ID NO: 37).

In still another embodiment, the agent is a peptide which sequence is comprised within the sequence of said pathogenic self-antigen; a peptide obtained by modification of said peptide, which modification consists in the replacement of one or more amino acid residues of the peptide by different amino acid residues (hereinafter "modified peptide"), said modified peptide still being capable of recognizing the T-cell receptor recognized by the parent peptide but with less affinity; or a nucleotide sequence encoding said pathogenic self-antigen, said peptide or said modified peptide.

In one embodiment, the agent is: (a) a peptide which sequence is comprised within the sequence of bovine IRBP (SEQ ID NO: 34); (b) a modified peptide as defined above obtained by modification of the peptide of (a); or (c) a nucleotide sequence encoding human or bovine IRPB, a peptide of (a), or a modified peptide of (b).

The peptide which sequence is comprised within the sequence of bovine IRBP (SEQ ID NO: 34) may be the peptide R16 (sequence 1177-1191 of IRBP), ADGSSWEGVGVVPDV (SEQ ID NO:38); the peptide PTARSVGAADGSSWEGVGVVPDV (SEQ ID NO:39); or the peptide HVDDTDLYLTIPTARSVGAADGS (SEQ ID NO:40).

In another embodiment, the agent is: (a) a peptide which sequence is comprised within the sequence of bovine S-Ag (SEQ ID NO:36); (b) a modified peptide as defined above obtained by modification of the peptide of (a); or (c) a nucleotide sequence encoding human or bovine S-Ag, a peptide of (a), or a modified peptide of (b).

The peptide (a) which sequence is comprised within the sequence of bovine S-Ag may be the peptide G-8 (sequence 347-354 of S-Ag) of the sequence TSSEVATE (SEQ ID NO:41); the peptide M-8 (sequence 307-314 of S-Ag), DTNLASST (SEQ ID NO:42; or the peptides of the sequences:

```
DTNLASSTIIKEGIDKTV;          (SEQ ID NO: 43)

VPLLANNRERRGIALDGKIKHE;      (SEQ ID NO: 44)

TSSEVATEVPFRLMHPQPED;        (SEQ ID NO: 45)

SLTKTLTLVPLLANNRERRG;        (SEQ ID NO: 46)

SLTRTLTLLPLLANNRERAG;        (SEQ ID NO: 47)

KEGIDKTVMGILVSYQIKVKL;       (SEQ ID NO: 48)
and

KEGIDRTVLGILVSYQIKVKL.       (SEQ ID NO: 49)
```

The modified peptide (c) derived from bovine S-Ag may be the G-8 analog, TSSEAATE (SEQ ID NO:50) or the M-8 analog, DTALASST (SEQ ID NO:51).

In another embodiment, the agent is a nucleotide sequence encoding a pathogenic self-antigen associated with a T-cell-mediated specific autoimmune disease of the eye, or a peptide or a modified peptide derived therefrom as defined herein.

In a further embodiment, the agent is T cells activated by Copolymer 1, or by a pathogenic self-antigen associated with a T-cell-mediated specific autoimmune disease of the eye, a peptide or a modified peptide derived therefrom as defined herein.

In yet a further embodiment, the agent is any combination of the agents defined above.

The invention further relates to the use of an agent selected from the agents defined herein for treatment of age-related macular degeneration or for the manufacture of a medicament for treatment of age-related macular degeneration.

When the agent is activated cells as described above, the cells can be preferably autologous or they can be from a matched donor and are preferably administered intravenously.

In one preferred embodiment, the agent is T cells activated by Copolymer 1, which can be prepared close to the administration step or cell banks can be established to store Copolymer 1-sensitized T cells for treatment of individuals at a later time, as needed. Autologous T cells may be obtained from the individual and allogeneic or semi-allogeneic T cells may obtained from a bank of stored T cells of each of the most common MHC-class II types are present. The patient is preferably treated with its autologous stored T cells, but if autologous T cells are not available, then cells should be used which share an MHC type II molecule with the patient, and these would be expected to be operable in that patient. The T cells are preferably stored in an activated state after exposure to Copolymer 1. However, the T cells may also be stored in a resting state and activated with Copolymer 1 once they are thawed and prepared for use.

The T cell lines are prepared in any way that is well known in the art. The cell lines of the bank are preferably cryopreserved. Once the cells are thawed, they are preferably cultured prior to injection in order to eliminate non-viable cells. During this culturing, the T cells can be activated or reactivated using the Copolymer 1 antigen as used in the original activation. Alternatively, activation may be achieved by culturing in the presence of a mitogen, such as phytohemagglutinin (PHA) or concanavalin A (preferably the former). This will place the cells into an even higher state of activation.

The bone marrow-derived myeloid cells for use in the present invention can be obtained from autologous or donor's peripheral blood or bone marrow and processed by techniques well-known in the art. The donor should be a matched, namely HLA-matched, donor. Once obtained, the myeloid cells may be cultured until they multiply to the level needed for transplant back into the patient and are then activated with the cytokine (IL-4, IL-13 or IFN-γ) for the time necessary to upregulate CD11c expression. For example, activation with up to 20 ng/ml IFN-γ may take 2-3 days until the peak of CD11c expression is reached.

In the examples, $CD11c^+$ microglia cells are described. Microglia are immune cells of the CNS that are derived from myeloid progenitor cells, which come from the bone marrow. Thus, microglia are the resident CNS cells whereas the bone marrow-derived myeloid cells are the infiltrating cells.

Pharmaceutical compositions/medicaments for use in accordance with the present invention may be formulated in conventional manner using one or more pharmaceutically/physiologically acceptable carriers or excipients, depending on the agent used. The carrier(s) must be "acceptable" in the sense of being compatible with the other ingredients of the composition and not deleterious to the recipient thereof.

Methods of administration and dosages will depend on the agent used and include, but are not limited to, parenteral, e.g., intravenous, intraperitoneal, intramuscular, subcutaneous, mucosal, e.g., oral, intranasal, buccal, vaginal, rectal, or intraocular, intrathecal, topical and intradermal routes, with or without adjuvant. Administration can be systemic or local.

The dosage of the agent to be administered will be determined by the physician according to the agent, the age of the patient and stage of the disease. For example, for Cop 1, the dosage may be chosen from a range of 1-80 mg, preferably 20 mg, although any other suitable dosage is encompassed by the invention. The treatment can be carried out by administration of repeated doses at suitable time intervals, according to the stage of the disease, the age and condition of the patient. In one embodiment, Cop 1 may be administered daily. In another preferred embodiment, the administration may be made according to a regimen suitable for immunization, for example, at least once a week, once a month or at least once every 2 or 3 months, or less frequently, but any other suitable interval between the immunizations is envisaged by the invention according to the condition of the patient.

When the agent is genetically engineered cells that produce IL-4, the cells are preferably engineered bone marrow-derived dendritic cells (DCs) that express IL-4, which may be obtained as described by Morita et al., 2001. Since DCs are specialized APCs that migrate from the periphery to lymphoid tissues, where they activate and regulate T cells, genetic modification of DCs to express immunoregulatory cytokines such as IL-4 provides a new immunotherapeutic strategy for treatment of AMD and other diseases.

The invention will now be illustrated by the following non-limiting examples.

EXAMPLES

Materials and Methods
  (i) Animals.
  Neonatal (P0-P1) mice, inbred adult male C57Bl/6J mice (8-10 weeks) were supplied by the Animal Breeding Center, Weizmann Institute of Science, Rehovot, Israel.
  (ii) Neural Progenitor Cell Culture.
  Coronal sections (2 mm thick) of tissue containing the subventricular zone of the lateral ventricle were obtained from the brains of adult C57Bl/6J mice. The tissue was minced and then incubated for digestion at 37° C., 5% $CO_2$ for 45 min in Earle's balanced salt solution containing 0.94 mg/ml papain (Worthington, Lakewood, N.J.) and 0.18 mg/ml of L-cysteine and EDTA. After centrifugation at 110×g for 15 min at room temperature, the tissue was mechanically dissociated by pipette trituration. Cells obtained from single-cell suspensions were plated (3500 cells/$cm^2$) in 75-$cm^2$ Falcon tissue-culture flasks (BD Biosciences, San Diego, Calif.), in neural stem/progenitor cell (NPC)-culturing medium [Dulbecco's modified Eagles's medium (DMEM)/F12 medium (Gibco/Invitrogen, Carlsbad, Calif.) containing 2 mM L-glutamine, 0.6% glucose, 9.6 μg/ml putrescine, 6.3 ng/ml progesterone, 5.2 ng/ml sodium selenite, 0.02 mg/ml insulin, 0.1 mg/ml transferrin, 2 μg/ml heparin (all from Sigma-Aldrich, Rehovot, Israel), fibroblast growth factor-2 (human recombinant, 20 ng/ml), and epidermal growth factor (human recombinant, 20 ng/ml; both from Peprotech, Rocky Hill, N.J.)]. Spheres were passaged every 4-6 days and replated as single cells. Green fluorescent protein (GFP)-expressing NPCs were obtained as previously described (Pluchino et al., 2003).
  (iii) Primary Microglial Culture.
  Brains from neonatal (P0-P1) C57Bl/6J mice were stripped of their meninges and minced with scissors under a dissecting microscope (Zeiss, Stemi DV4, Germany) in Leibovitz-15 medium (Biological Industries, Kibbutz Beit Ha-Emek, Israel). After trypsinization (0.5% trypsin, 10 min, 37° C./5% $CO_2$), the tissue was triturated. The cell suspension was washed in culture medium for glial cells [DMEM supplemented with 10% fetal calf serum (FCS; Sigma-Aldrich, Rehovot), L-glutamine (1 mM), sodium pyruvate (1 mM), penicillin (100 U/ml), and streptomycin (100 mg/ml)] and cultured at 37° C./5% $CO_2$ in 75-$cm^2$ Falcon tissue-culture flasks (BD Biosciences) coated with poly-D-lysine (PDL) (10 mg/ml; Sigma-Aldrich, Rehovot) in borate buffer (2.37 g borax and 1.55 g boric acid dissolved in 500 ml sterile water, pH 8.4) for 1 h, then rinsed thoroughly with sterile, glass-distilled water. Half of the medium was changed after 6 h in culture and every $2^{nd}$ day thereafter, starting on day 2, for a total culture time of 10-14 days. Microglia were shaken off the primary mixed brain glial cell cultures (150 rpm, 37° C., 6 h) with maximum yields between days 10 and 14, seeded ($10^5$ cells/ml) onto PDL-pretreated 24-well plates (1 ml/well; Corning, N.Y., N.Y.), and grown in culture medium for microglia [RPMI-1640 medium (Sigma-Aldrich, Rehovot) supplemented with 10% FCS, L-glutamine (1 mM), sodium pyruvate (1 mM), β-mercaptoethanol (50 mM), penicillin (100 U/ml), and streptomycin (100 mg/ml)]. The cells were allowed to adhere to the surface of a PDL-coated culture flask (30 min, 37° C./5% $CO_2$), and non-adherent cells were rinsed off.

(iv) Immunocytochemistry and Immunocyhistochemistry.

Primary antibodies: *Bandeiraea simplicifolia* isolectin B4 (IB-4; 1:50; Sigma-Aldrich, Rehovot); mouse anti-β-tubulin (anti-βIII-T) isoform C-terminus antibodies (1:500; Chemicon, Temecula, Calif.), rat anti-CD11b (MAC1; 1:50; BD—Pharmingen, Franklin Lakes, N.J.), hamster anti-CD11c (1:100; eBioscience, San Diego, Calif.), rat anti-MHC-II Abs (clone IBL-5/22; 1:50), mouse anti-Aβ (human amino-acid residues 1-17; clone 6E10; Chemicon), rat anti-BrdU (1:200; Oxford Biotechnology, Kidlington, Oxfordshire, UK), goat anti-doublecortin (anti-DCX) (1:400; Santa Cruz Biotechnology, Santa Cruz, Calif.), mouse anti-neuronal nuclear protein (NeuN; 1:200; Chemicon), goat anti-IGF-I Abs (1:20; R&D Systems), goat anti-TNF-α Abs (1:100; R&D Systems), rabbit anti-CD3 polyclonal Abs (1:100; DakoCytomation, CA). Secondary antibodies: FITC-conjugated donkey anti-goat, Cy-3-conjugated donkey anti-mouse, and Cy-3- or Cy-5-conjugated donkey anti-rat, biotin-conjugated anti-hamster antibody and Cy-3- or Cy-5-conjugated streptavidin antibody (all from Jackson ImmunoResearch).

Cover slips from co-cultures of NPCs and mouse microglia were washed with PBS, fixed as described above, treated with a permeabilization/blocking solution containing 10% FCS, 2% bovine serum albumin, 1% glycine, and 0.1% Triton X-100 (Sigma-Aldrich, Rehovot), and stained with a combination of mouse anti-O-tubulin (anti-βIII-T) isoform C-terminus antibodies (1:500; Chemicon, Temecula, Calif.), rat anti-CD11b (MAC1; 1:50; BD—Pharmingen, Franklin Lakes, N.J.) and hamster anti-CD11c (1:100; eBioscience, San Diego, Calif.). To capture the microglia FITC- or Cy3-conjugated *Bandeiraea simplicifolia* isolectin B4 (IB-4; 1:50; Sigma-Aldrich, Rehovot) was used. To detect expression of human Aβ anti-Aβ (human amino-acid residues 1-17) (mouse, clone 6E10; Chemicon) was used.

For BrdU staining, sections were washed with PBS and incubated in 2N HCl at 37° C. for 30 min. Sections were blocked for 1 h with blocking solution [PBS containing 20% normal horse serum and 0.1% Triton X-100, or PBS containing mouse immunoglobulin blocking reagent obtained from Vector Laboratories (Burlingame, Calif.)].

For immunohistochemistry, tissue sections were treated with a permeabilization/blocking solution containing 10% FCS, 2% bovine serum albumin, 1% glycine, and 0.05% Triton X-100 (Sigma-Aldrich, St. Louis). Tissue sections were stained overnight at 4° C. with specified combinations of the following primary antibodies: rat anti-BrdU (1:200; Oxford Biotechnology, Kidlington, Oxfordshire, UK), goat anti-doublecortin (anti-DCX) (1:400; Santa Cruz Biotechnology, Santa Cruz, Calif.), and mouse anti-neuronal nuclear protein (anti-NeuN) (1:200; Chemicon). Secondary antibodies were FITC-conjugated donkey anti-goat, Cy-3-conjugated donkey anti-mouse, and Cy-3- or Cy-5-conjugated donkey anti-rat (1:200; Jackson ImmunoResearch, West Grove, Pa.). CD11b (MAC1; 1:50; BD—Pharmingen) or FITC-conjugated 113-4 was used for labeling of microglia. Anti-MHC-II Abs (rat, clone IBL-5/22; 1:50) was used to detect expression of cell-surface MHC-II proteins. To detect expression of CD11c hamster anti-CD11c (1:100; eBioscience, San Diego, Calif.) was used. Anti-Aβ (human amino-acid residues 1-17) (mouse, clone 6E10; Chemicon) was used to detect expression of human Aβ. Expression of IGF-I was detected by goat anti-IGF-I Abs (1:20; R&D Systems). Expression of TNF-α was detected by goat anti-TNF-α Abs (1:100; R&D Systems). T cells were detected with anti-CD3 polyclonal Abs (rabbit, 1:100; DakoCytomation, CA). Propidium iodide (1 μg/ml; Molecular Probes, Invitrogen, Carlsbad, Calif.), was used for nuclear staining.

Control sections (not treated with primary antibody) were used to distinguish specific staining from staining of nonspecific antibodies or autofluorescent components. Sections were then washed with PBS and cover-slipped in polyvinyl alcohol with diazabicyclo-octane as anti-fading agent.

(v) Transgenic Mice.

Nineteen adult double-transgenic $APP_{K595N,\ M596L}+PS1_{\Delta E9}$ mice of the B6C3-Tg (APPswe, PSEN1dE9) 85 Dbo/J strain (Borchelt et al., 1997) were purchased from The Jackson Laboratory (Bar Harbor, Me.) and were bred and maintained in the Animal Breeding Center of The Weizmann Institute of Science. All animals were handled according to the regulations formulated by the Weizmann Institute's Animal Care and Use Committee, and all experiments and procedures were approved by the Weizmann Institute's Animal Care and Use Committee.

(vi) Genotyping.

All mice used in this experiment were genotyped for the presence of the transgenes by PCR as previously described (Jankowsky et al., 2004).

(vii) Reagents.

Recombinant mouse IFN-γ and IL-4 were obtained from R&D Systems (Minneapolis, Minn.). β-amyloid peptide [fragment 1-40 ($A\beta_{1-40}$)] was purchased from Sigma-Aldrich, St. Louis, Mo. The Aβ peptide was dissolved in endotoxin-free water, and Aβ aggregates were formed by incubation of Aβ, as described (Butovsky et al., 2005).

(viii) Copolymer-1 Vaccination.

Each mouse was subcutaneously injected five times with a total of 100 μg of high-molecular-weight (TV-5010 DS, from batch no. 486220205; Teva Pharmaceutical Industries, Petach Tikva, Israel) emulsified in 200 μl PBS, from experimental day 0 until day 24, twice during the first week and once a week thereafter.

(ix) Behavioral Testing.

Spatial learning/memory was assessed by performance on a hippocampus-dependent visuo-spatial learning task in the Morris water maze (MWM) and carried out as described (Lichtenwalner et al., 2001).

(x) Administration of 5-Bromo-2'-Deoxyuridine and Tissue Preparation.

The cell-proliferation marker 5-bromo-2'-deoxyuridine (BrdU) was dissolved by sonication in phosphate-buffered saline (PBS) and injected intraperitoneally (i.p.) into each mouse (50 mg/kg body weight; 1.25 mg BrdU in 200 μl PBS). Starting from experimental day 22 after the first Cop-1 vaccination, BrdU was injected i.p. twice daily, every 12 h for 2.5 days, to label proliferating cells. Three weeks after the first BrdU injection the mice were deeply anesthetized and perfused transcardially, first with PBS and then with 4% paraformaldehyde. The whole brain was removed, postfixed overnight, and then equilibrated in phosphate-buffered 30% sucrose. Free-floating 30-μm sections were collected on a freezing microtome (Leica SM2000R) and stored at 4° C. prior to immunohistochemistry.

(xi) Co-Culturing of Neural Progenitor Cells and Microglia.

Cultures of treated or untreated microglia were washed twice with fresh NPC-differentiation medium (same as the culture medium for NPCs but without growth factors except for 0.02 mg/ml insulin and with 2.5% FCS) to remove all traces of the tested reagents, then incubated on ice for 15 min and shaken at 350 rpm for 20 min at room temperature. Microglia were removed from the flasks and immediately co-cultured ($5 \times 10^4$ cells/well) with NPCs ($5 \times 10^4$ cells/well) for 10 days on cover slips coated with Matrigel™ (BD Biosciences) in 24-well plates, in the presence of NPC-differentiation medium. The cultures were then fixed with 2.5% paraformaldehyde in PBS for 30 min at room temperature and stained for neuronal and glial markers.

(xii) Quantification and Stereological Counting Procedure.

A Zeiss LSM 510 confocal laser scanning microscope (×40 magnification) was used for microscopic analysis. For experiments in vitro fields of 0.053 mm² (n=8-16 from at least two different cover slips) were scanned for each experimental group. For each marker, 500-1000 cells were sampled. Cells co-expressing GFP and βIII-T were counted.

For in-vivo experiments, the numbers of Aβ plaques and CD11b$^+$ microglia in the hippocampus were counted at 300-μm intervals in 6-8 coronal sections (30 μm) from each mouse. Neurogenesis in the dentate gyrus was evaluated by counting of pre-mature neurons (DCX$^+$), proliferating cells (BrdU$^+$), and newly formed mature neurons (BrdU$^+$/NeuN$^+$) in six coronal sections (370 μm apart) per mouse brain. To obtain an estimate of the total number of labeled cells per dentate gyrus, the total number of cells counted in the selected coronal sections from each brain was multiplied by the volume index (the ratio between the volume of the dentate gyrus and the total combined volume of the selected sections). Specificity of BrdU+/NeuN+ co-expression was assayed using the confocal microscope (LSM 510) in optical sections at 1-μm intervals. Quantification of CD3$^+$, CD11b$^+$ and CD11c$^+$ cells were analyzed from 30-50 Aβ-plaques of each mouse tested in this study. Cell counts, numbers of Aβ plaques, plaque areas, and intensity of NeuN staining per unit area in the dentate gyrus were evaluated automatically using Image-Pro Plus 4.5 software (Media Cybernetics, Carlsbad, Calif.).

(xiii) Statistical Analysis.

MWM behavior scores were analyzed using 3-way ANOVA. Treatment group and trial block were used as sources of variation to evaluate the significance of differences between mean scores during acquisition trial blocks in the MWM. When the P-value obtained was significant, a pairwise Fisher's least-significant-difference multiple comparison test was run to determine which groups were significantly different.

The in-vitro results were analyzed by two-tailed unpaired Student's t-test and by the Tukey-Kramer multiple comparisons test (ANOVA) and are expressed as means±SEM. Results in vivo were analyzed by two-tailed unpaired Student's t-test or 1-way ANOVA and are expressed as means±SEM.

Example 1

Aggregated β-Amyloid Induces Microglia to Express a Phenotype that Blocks Neurogenesis, and the Blocking is Counteracted by IL-4

Figure 1B:
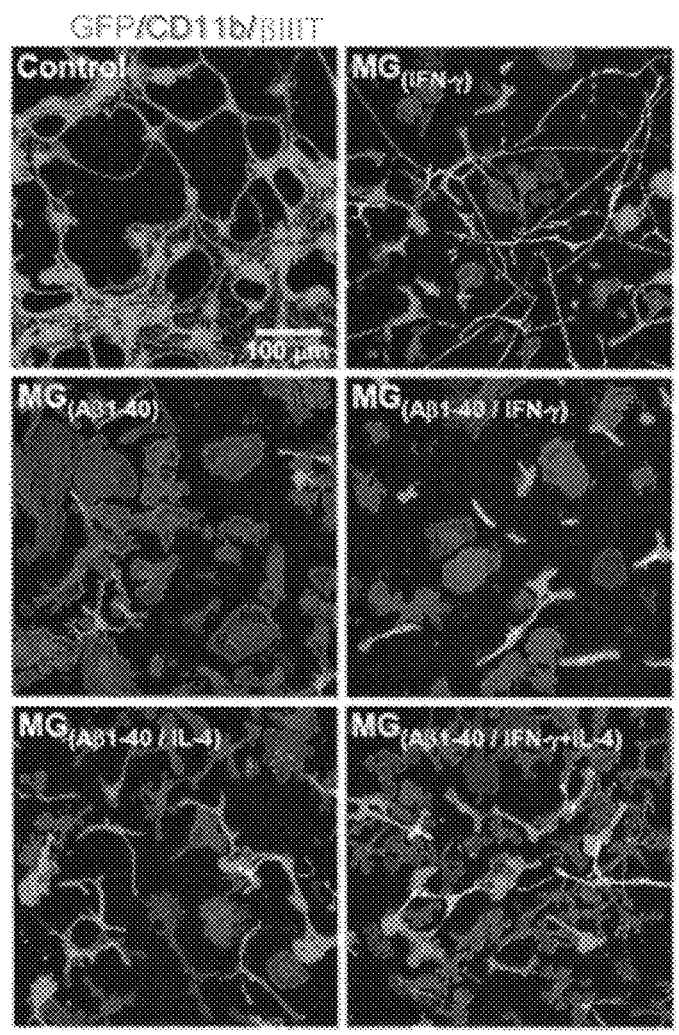
Figure 1C:
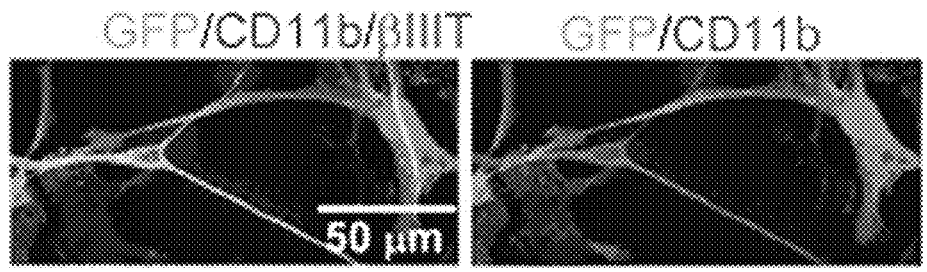
Figure 1D:
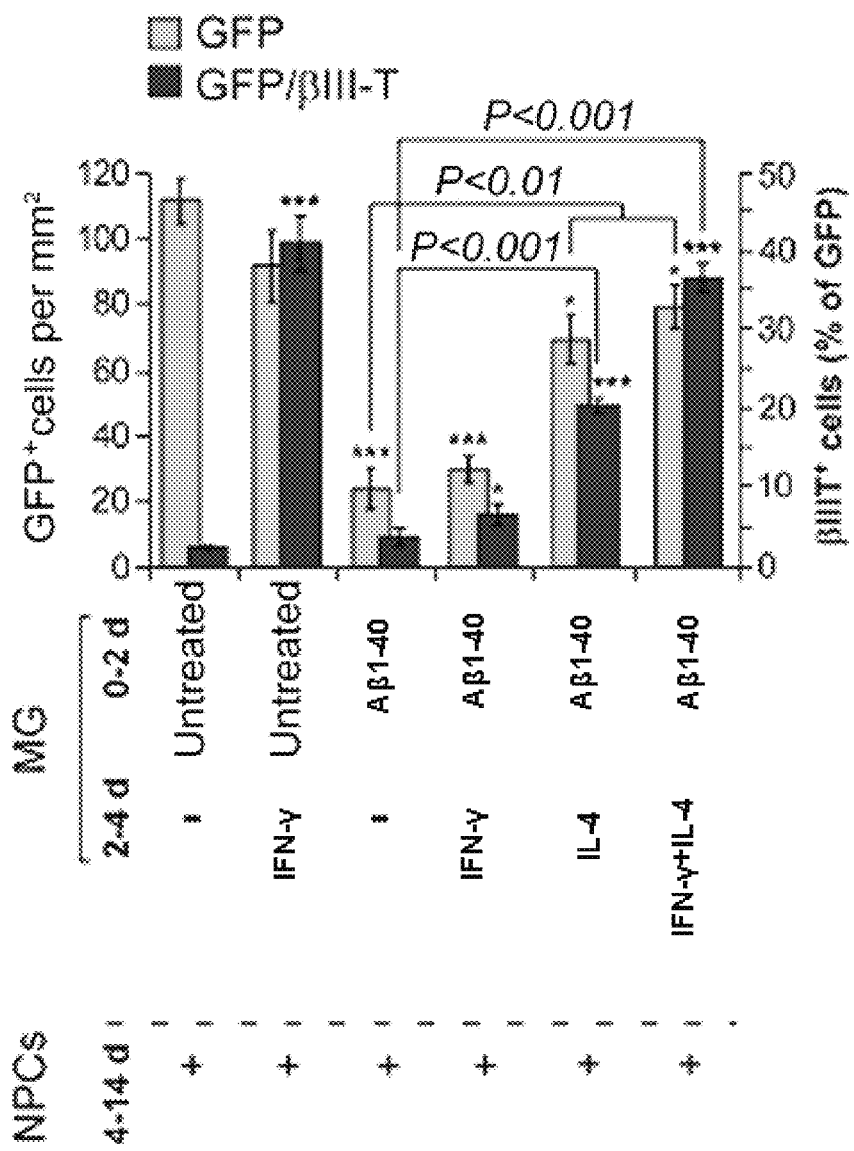

Previous in vitro findings from our laboratory have suggested that the microglia found in association with inflammatory and neurodegenerative diseases (e.g. microglia activated by LPS or by aggregated A$\beta_{(1-40)}$) have an impaired ability to present antigen, whereas IL-4-activated microglia, shown to be associated with neural tissue survival, express MHC-II, produce IGF-I, and decrease TNF-α, expression (Butovsky et al., 2005). Here we first examined whether Aβ-activated microglia block neurogenesis, and if so, whether T cell-derived cytokines can counteract the inhibitory effect. To this end we co-cultured green fluorescent protein (GFP)-expressing neural stem/progenitor cells (NPCs) with microglia that had been pre-incubated for 48 h in their optimal growth medium (Butovsky et al., 2005) in the presence or absence of the aggregated Aβ peptide 1-40 (A$\beta_{(1-40)}$; 5 μM) and subsequently treated for an additional 48 h with IFN-γ (10 ng/ml) or IL-4 (10 ng/ml) or IL-4 together with IFN-γ (10 ng/ml). The choice of A$\beta_{(1-40)}$ rather than A$\beta_{(1-42)}$ and its concentration was based on our previous demonstration that this compound induces cytotoxic activity in microglia (Butovsky et al., 2005). Growth media and cytokine residues were then washed off the co-cultured microglia, and each of the treated microglial preparations was freshly co-cultured with dissociated adult subventricular zone-derived NPC spheres (Butovsky et al., 2006a) on coverslips coated with Matrigel™ in the presence of differentiation medium (Butovsky et al., 2006a) (FIG. 1A). Expression of GFP by NPCs confirmed that any differentiating neurons seen in the cultures were derived from the NPCs rather than from contamination of the primary microglial culture. After 10 days, we could discern a few GFP-positive NPCs expressing the neuronal marker βIII-T in microglia-free cultures (control). In co-cultures of NPCs with microglia previously activated by incubation with IFN-γ (10 ng/ml; MG$_{(IFN-\gamma)}$) a dramatic increase in numbers of GFP$^+$/βIII-T$^+$ cells was seen. On the contrary, microglia activated by aggregated A$\beta_{(1-40)}$ (MG$_{(A\beta1-40)}$) blocked neurogenesis and decreased the number of NPCs. The addition of IFN-γ to Aβ-activated microglia (MG$_{(A\beta1-40/IFN-\gamma)}$), failed to reverse their negative effect on neurogenesis. In contrast, the addition of IL-4 (10 ng/ml) to microglia pretreated with aggregated A$\beta_{(1-40)}$ (MG$_{(A\beta1-40/IL-4)}$) partially counteracted the adverse effect of the aggregated Aβ on NPCs survival and differentiation, with the result that these microglia were able to induce NPCs to differentiate into neurons. However, when IFN-γ was added in combination with IL-4 (MG$_{(A\beta1-40/IFN-\gamma+IL-4)}$), their effect in counteracting the negative activity of the Aβ-activated microglia on NPC survival and differentiation was stronger than the effect of IL-4 alone (FIG. 1B). We verified that in all cases the βIII-T$^+$ cells also expressed GFP (FIG. 1C). This finding is particularly interesting in view of our earlier demonstration that the order in which threatening stimuli are presented to the microglia critically affects the ability of these cells to withstand them (Butovsky et al., 2005). The quantitative analysis presented in FIG. 1D summarizes the data shown in FIG. 1B, and in addition shows that differentiation in the presence of untreated microglia occurred only to a small extent. Notably, no βIII-T$^+$ cells were seen in microglia cultured without NPCs (Butovsky et al., 2006a).

Example 2

T-Cell-Based Vaccination with Copolymer-1 Modulates Immune Activity of Microglia, Eliminates β-Amyloid Plaque Formation, and Induces Neurogenesis The above findings prompted us to examine whether a T cell-based vaccination would alter the default microglial phenotype in Alzheimer's disease and hence lead to plaque removal and neurogenesis. The antigen we chose for the vaccination was Cop-1 (Teitelbaum et al., 1996), shown by us to be weakly cross-reactive with a wide-range of CNS autoantigens and, depending on the regimen, to be neuroprotective under conditions of both acute and chronic neurodegeneration (Kipnis et al., 2000; Schori et al., 2001; Angelov et al., 2003). We examined the effect of Cop-1 in Tg-AD mice, suffering from learning/memory impairment and an accumulation of aggregated Aβ plaques deposited mainly in the cortex and the hippocampus, both characteristic features of early-onset familial Alzheimer's disease (Borchelt et al., 1997). The regimen for Cop-1 administration was similar to that used to evoke neuroprotection in a model of chronic elevation of intraocular pressure (Bakalash et al., 2005).

Figure 2A:
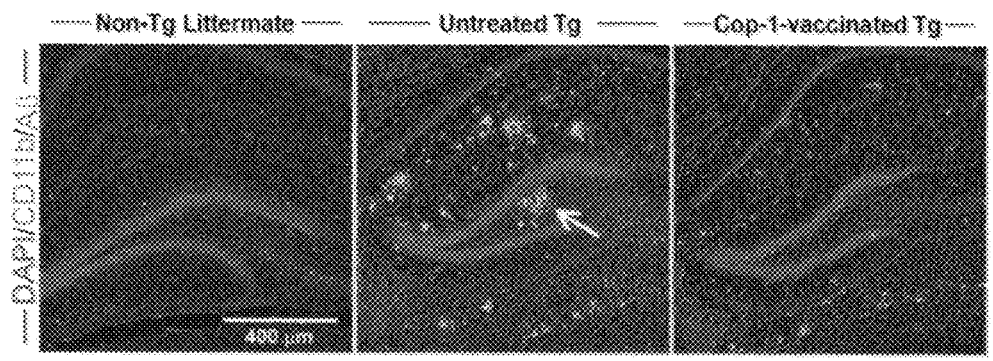
FIGS. 2A-2L show that Cop-1 vaccination leads to reduction in β-amyloid and counteracts loss of hippocampal neurons in the brains of transgenic Alzheimer's disease mice: key role of microglia.

We verified the presence of both transgenes in each mouse by PCR amplification of genomic DNA. Tg-AD mice aged approximately 8 months were then vaccinated subcutaneously with Cop-1 (n=6) twice during the first week and once a week thereafter. Age-matched untreated Tg-AD mice (n=7) and non-Tg littermates (n=6) served, respectively, as untreated-Tg and wild-type controls. Seven weeks after the first Cop-1 injection all the mice were euthanized and analyzed. Staining of brain cryosections from Tg-AD mice with antibodies specific to human Aβ disclosed numerous plaques in the untreated-Tg-AD mice but very few in the Tg-AD mice vaccinated with Cop-1 (FIG. 2A). No plaques were seen in their respective non-Tg littermates (FIG. 2A).

Figure 2B:
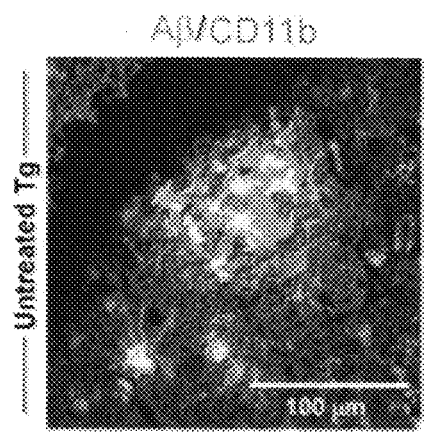
Figure 2C:
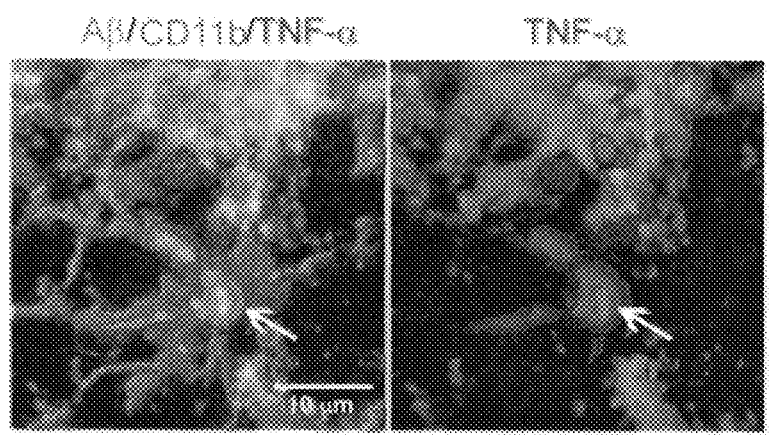
Figure 2D:
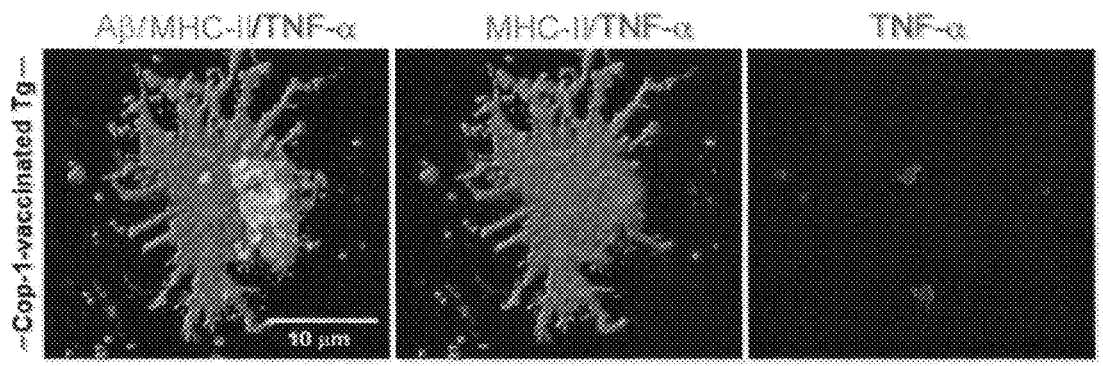
Figure 2E:
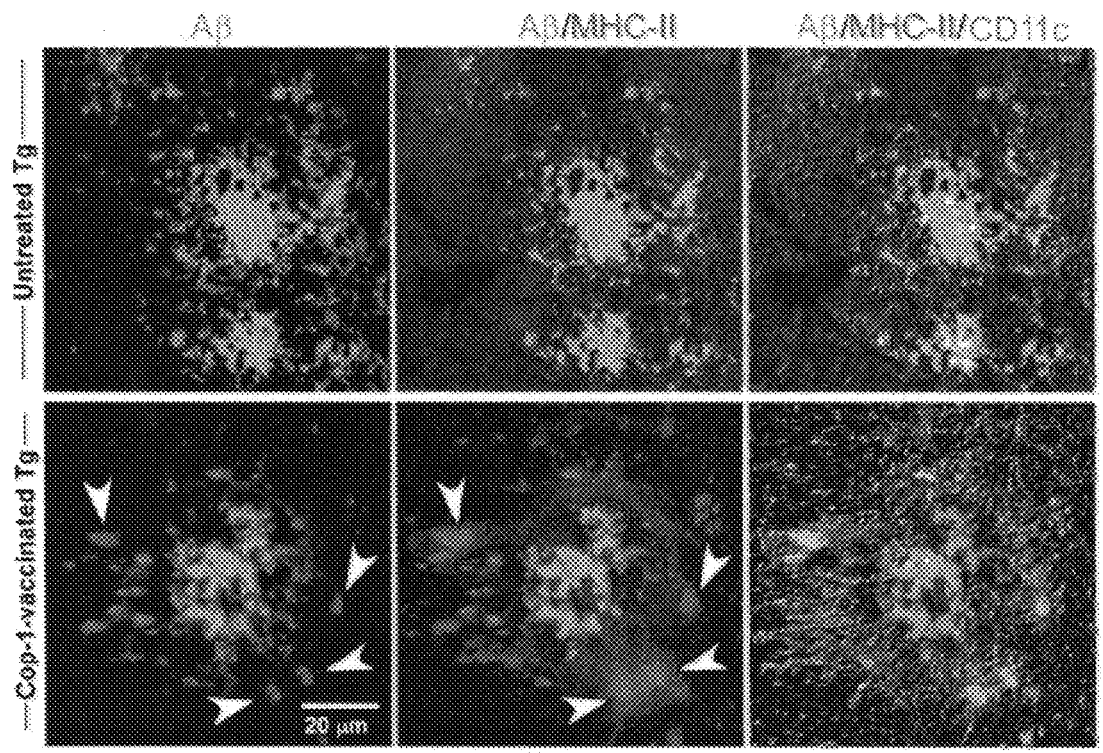

The above results, coupled with the in-vitro findings, prompted us to look for changes in microglial features in the vaccinated Tg-AD mice. Plaques in the untreated-Tg-AD mice were found to be associated with the abundant appearance of CD11b$^+$ microglia (FIG. 2A and FIG. 2B) expressing TNF-α (FIG. 2C). Fewer CD11b$^+$ microglia were detectable in the Cop-1-vaccinated Tg-AD mice (FIG. 2A). It is important to note that the CD11b$^+$ microglia in the untreated-Tg-AD mice showed relatively few ramified processes FIG. 2C). Staining with anti-MHC-II antibodies disclosed that in the Cop-1-vaccinated Tg-AD mice most of the microglia adjacent to residual Aβ plaques expressed MHC-II, and hardly any of them expressed TNF-α (FIG. 2D), whereas in the untreated-Tg-AD mice hardly any microglia expressed MHC-II (FIG. 2E), suggesting that their ability to function as APCs is limited. All of the MHC-II$^+$ cells were co-labeled with IB-4 (data not shown), verifying their identification as microglia. The dendritic-like morphology (FIG. 2D) of the MHC-II$^+$ microglia seen in the Cop-1-vaccinated Tg-AD mice encouraged us to examine whether they express the characteristic marker of dendritic cells, namely CD11c. CD11c$^+$ microglia in untreated Tg-AD mice were only rarely found in association with Aβ$^+$ plaques, whereas any residual Aβ-stained plaques seen in the Cop-1-vaccinated mice were surrounded by MHC-II$^+$/CD11c$^+$ microglia (FIG. 2E). Notably, these CD11c$^+$ microglia were also positively stained for CD11b (FIG. 3A); in addition, they were loaded with Aβ, indicative of their engulfment of this peptide (FIG. 2E). Quantitative analysis revealed that the number of CD11b$^+$ cells associated with Aβ-plaque significantly decreased in the Cop-1-vaccinated Tg-AD mice (FIG. 3B), and that as a result of the vaccination 87% of the CD11b$^+$ became CD11b$^+$/CD11c$^+$ cells relative to 25% in the untreated Tg-AD mice (FIG. 3C).

Figure 2F:
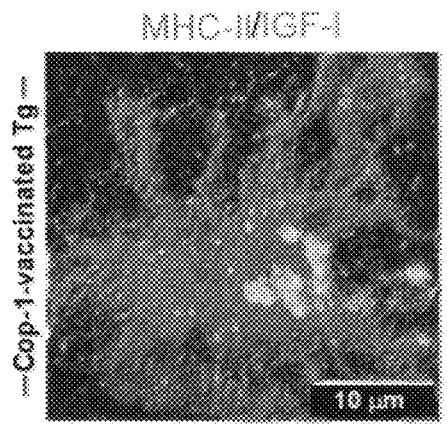
Figure 2G:
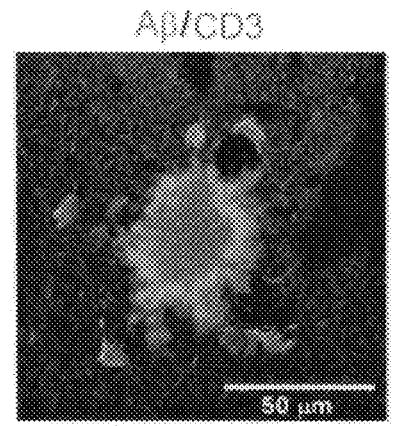
Figure 2H:
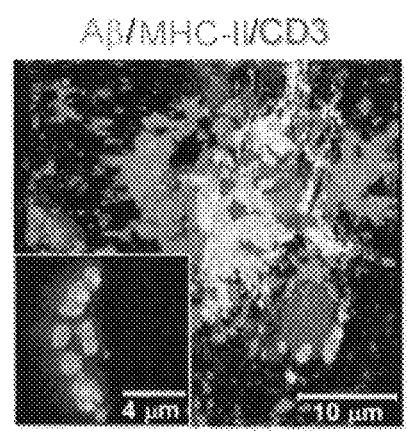
Figure 2I:
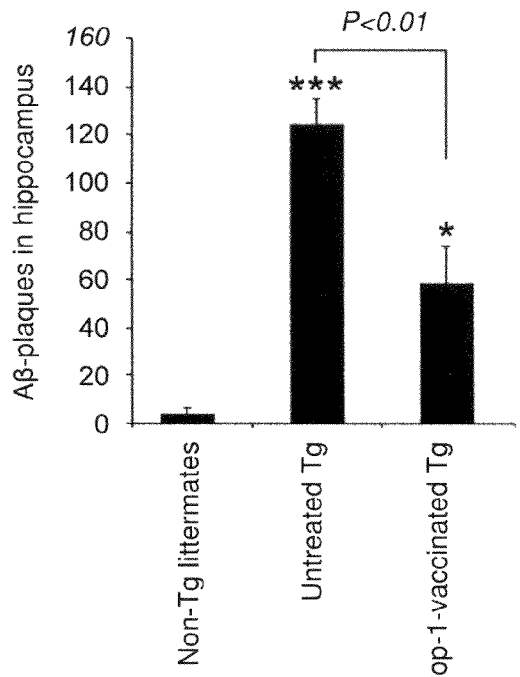
Figure 2J:
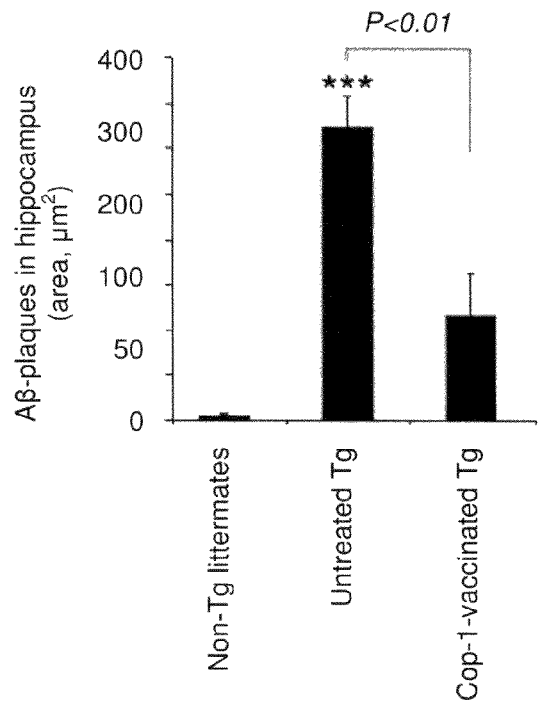
Figure 2K:
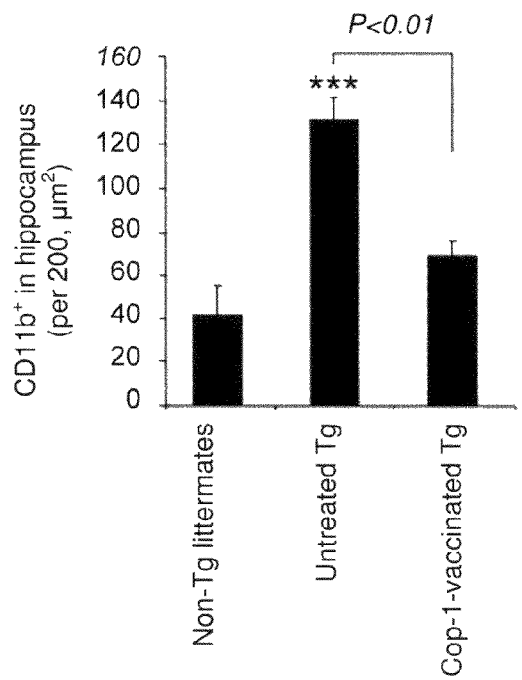
Figure 2L:
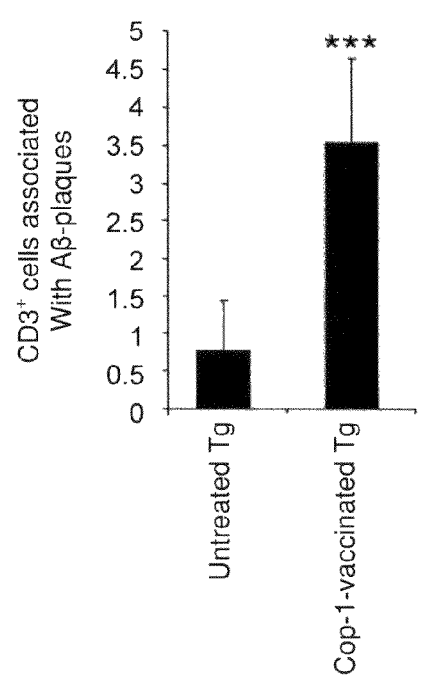

In view of our recent finding that MHC-II$^+$ microglia (which are activated by IL-4) abundantly express IGF-I (Butovsky et al., 2005; Butovsky et al., 2006a;b), we examined IGF-I expression in the vaccinated Tg-AD mice. MHC-II$^+$ microglia in these mice were indeed found to express IGF-I (FIG. 2F). Staining for the presence of T cells, identified by anti-CD3 antibodies, revealed that unlike in the untreated-Tg-AD mice, in the Cop-1-vaccinated Tg-AD mice there were numerous T cells associated with Aβ-plaques (FIG. 2G). Moreover, most of the T cells in the Cop-1 vaccinated Tg-AD mice were found to be located close to MHC-II$^+$ microglia. Any Aβ-immunoreactivity detected in those mice appeared to be associated with the MHC-II$^+$ microglia, suggesting the occurrence of an immune synapse between these microglia and CD3$^+$ T cells (FIG. 2H). Quantitative analysis confirmed the presence of significantly fewer plaques in the Cop-1-vaccinated Tg-AD mice than in the untreated-Tg-AD mice (FIG. 2I), and showed that the area occupied by the plaques was significantly smaller in the vaccinated Tg-AD mice than in their age-matched untreated counterparts (FIG. 2J). In addition, significantly fewer CD11b$^+$ microglia (FIG. 2K) and significantly more T cells associated with Aβ-plaque were observed in the Cop-1-vaccinated Tg-AD mice than in the corresponding groups of untreated-Tg-AD mice (FIG. 2L).

Figure 4A:
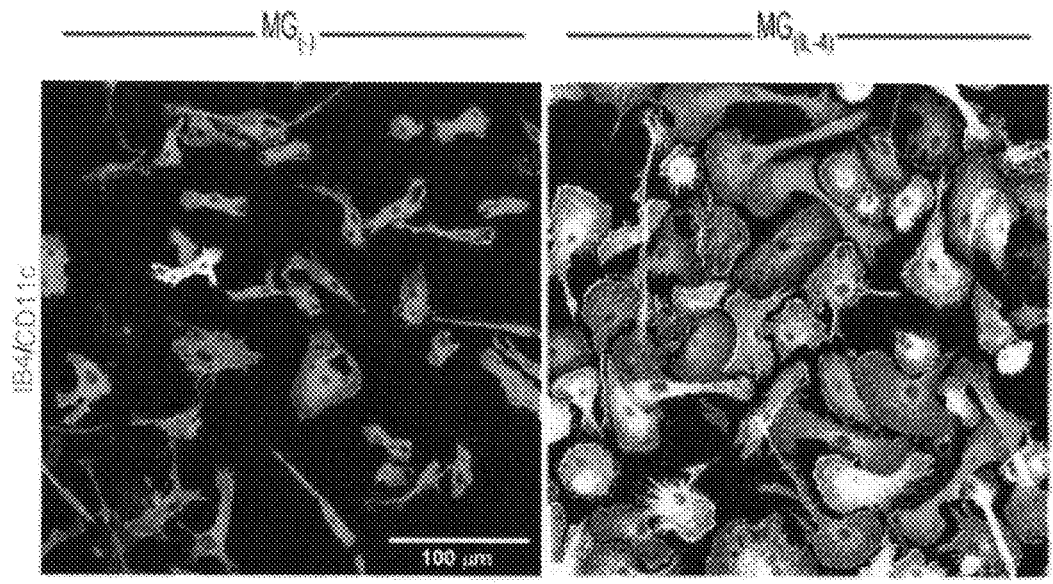
FIGS. 4A-4D show that Cop-1 vaccination induces microglia to express CD11c: role of IL-4.
Figure 4B:
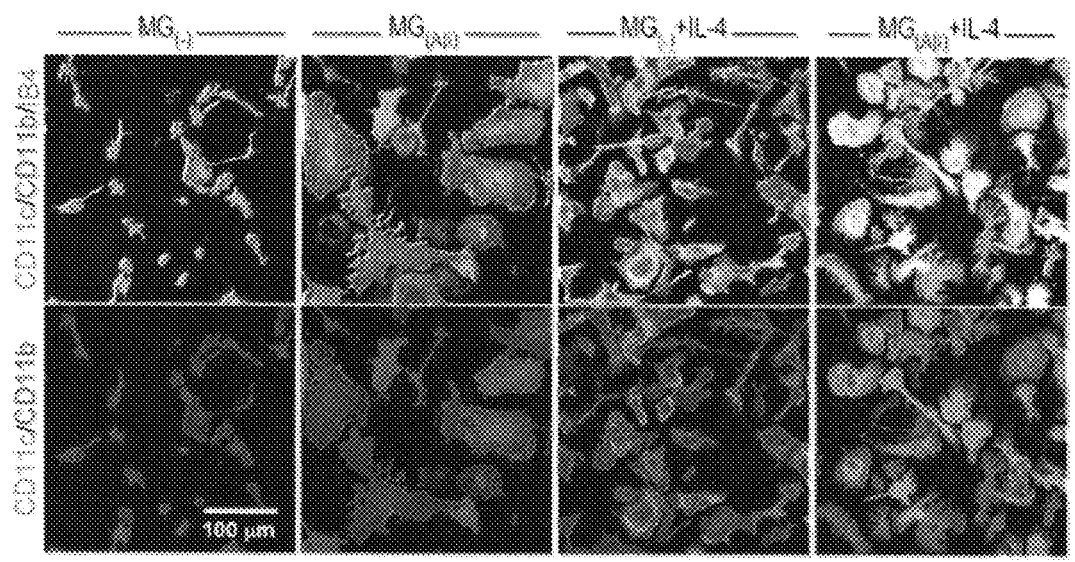
Figure 4C:
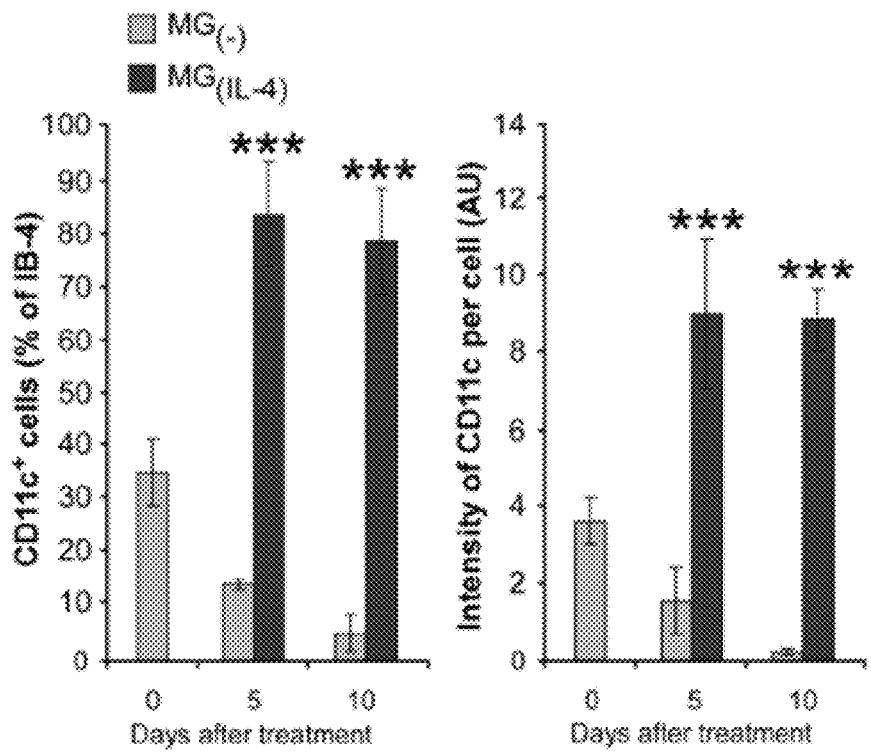
Figure 4D:
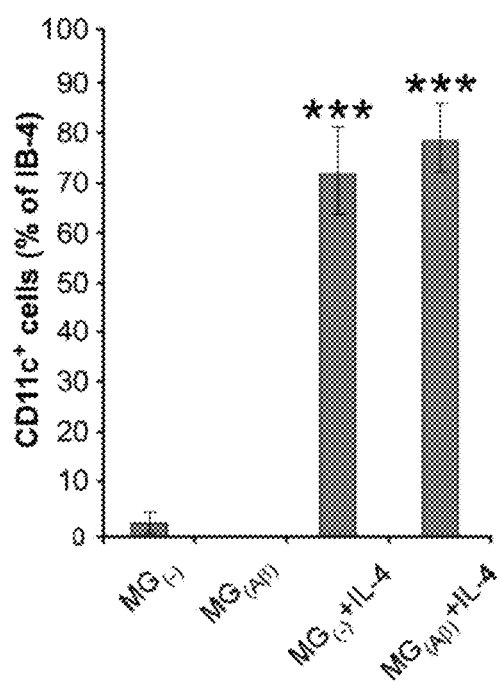

On the basis of our previous findings, we suspected that the switch from a CD11b$^+$/CD11c$^-$/IGF-1$^-$ to a CD11b$^+$/CD11c$^+$/IGF-I$^+$ microglial phenotype in the Cop-1 vaccinated Tg-AD mice might be attributable to IL-4. We examined this possibility in vitro. Staining of 5-day microglia cultures with the CD11c marker showed that CD11c was hardly expressed at all by untreated, but was abundantly expressed by microglia activated by IL-4 (FIG. 4A). Moreover, IL-4, even if only added 3 days after the microglia were exposed to Aβ, was able to induce them to express CD11c (FIG. 4B). Differential activation of the microglia was also reflected in morphological differences: microglia activated by Aβ exhibited amoeboid morphology, whereas the rounded shape of the CD11c$^+$ microglia was reminiscent of dendritic cells (FIG. 4B). Most importantly, the amoeboid morphology of the Aβ-stained microglia was reversible on addition of IL-4, when they again took on the morphological appearance of dendritic-like cells (FIG. 4B). The various treatments applied to the microglia did not affect their expression of CD11b, suggesting that they did not lose their CD11b characteristics when they took on the expression of CD11c (FIG. 4B). Quantitative analysis of CD11c expression, assessed by the number of CD11c$^+$ cells and the intensity of their staining as a function of time in culture, revealed that soon after seeding (day 0) untreated microglia expressed low levels of CD11c, which gradually disappeared (FIG. 4C). In contrast, the expression of CD11c induced by IL-4 was not transient. Quantification of the ability of IL-4 to induce CD11c expression even after the microglia were pretreated with Aβ is shown in FIG. 4D.

Figure 5A:
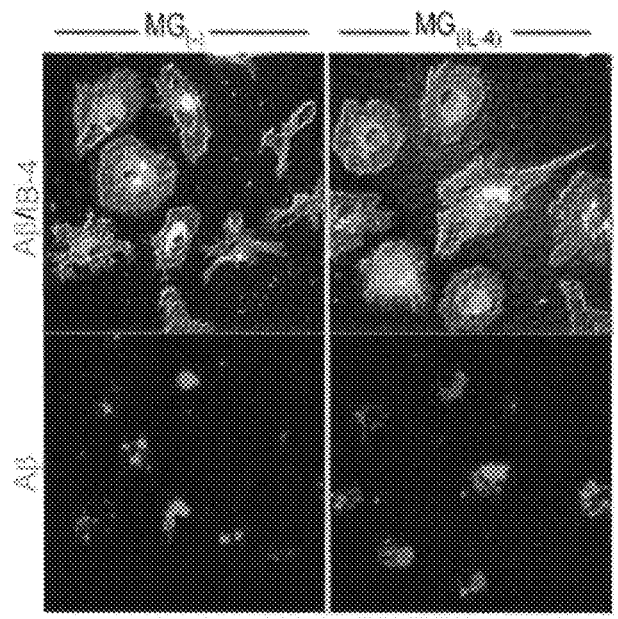
FIGS. 5A-5B show engulfment of aggregated Aβ by activated microglia. Microglia were treated with IL-4 (10 ng/ml) 24 h after seeding ($MG_{(IL-4)}$) or were left untreated for 48 h ($MG_{(-)}$). The media were then replaced by a labeling medium (DMEM containing 10 mg/ml bovine serum albumin), and aggregated $Aβ_{(1-40)}$ was added (5 μg/ml) for 1 h. Following incubation the cultures were fixed and immunostained with antibodies directed to human Aβ and co-stained for microglia (IB-4).
Figure 5B:
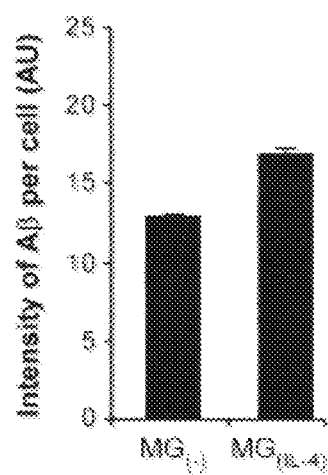

The correlation between the phenotype that was found to be induced by the Cop-1 vaccination and the IL-4 effect on microglia in vitro prompted us to examine the ability of IL-4-activated microglia to phagocytize aggregated Aβ$_{(1-40)}$. Quantitative comparison (by intracellular staining) of immunoreactive Aβ engulfed by IL-4-treated and untreated microglia indicated that IL-4 did not interfere with the ability of microglia to engulf Aβ (FIG. 5).

Figure 6A:
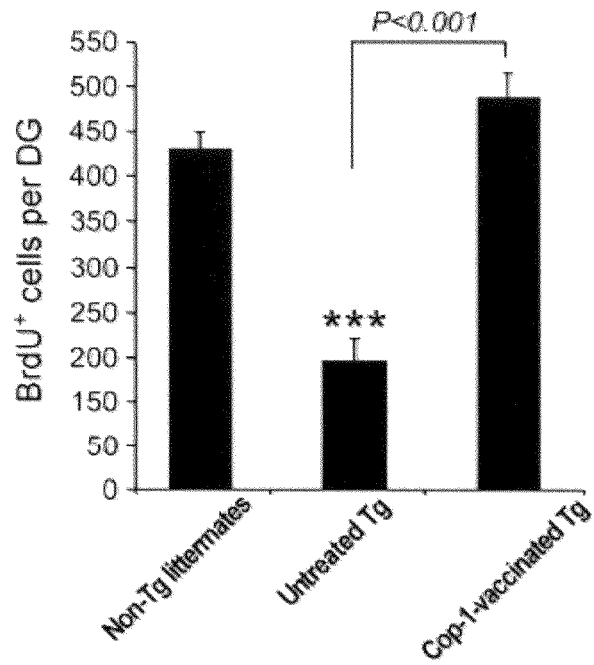
FIGS. 6A-6E depict enhanced neurogenesis induced by Cop-1 vaccination in the hippocampal dentate gyri of adult transgenic (Tg) AD mice. Three weeks after the first Cop-1 vaccination, mice in each experimental group were injected i.p. with 5-bromo-2'-deoxyuridine (BrdU) twice daily for 2.5 days. Three weeks after the last injection their brains were excised and the hippocampi analyzed for BrdU, DCX (a marker of early differentiation of the neuronal lineage), and NeuN (a marker of mature neurons).
Figure 6B:
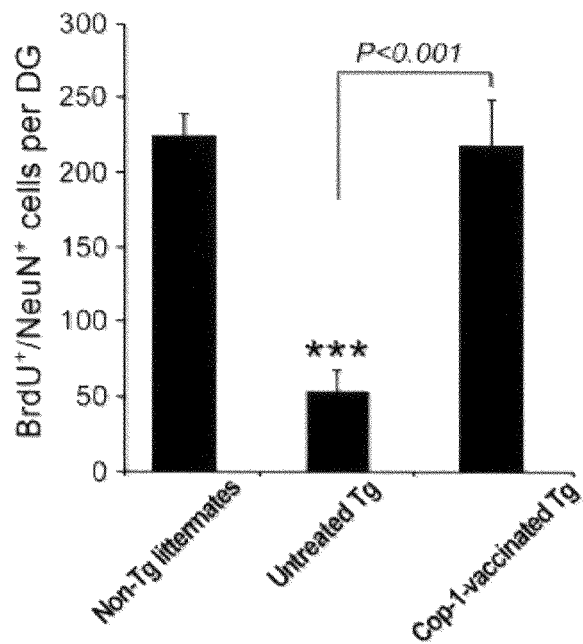
Figure 6C:
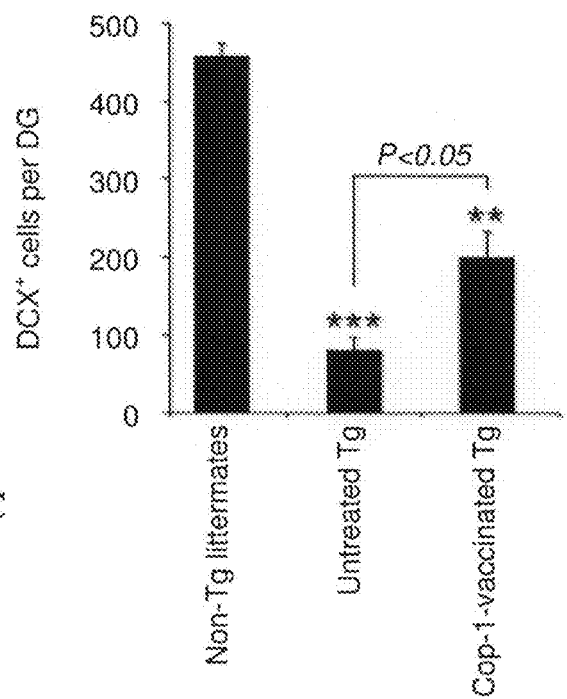
Figure 6D:
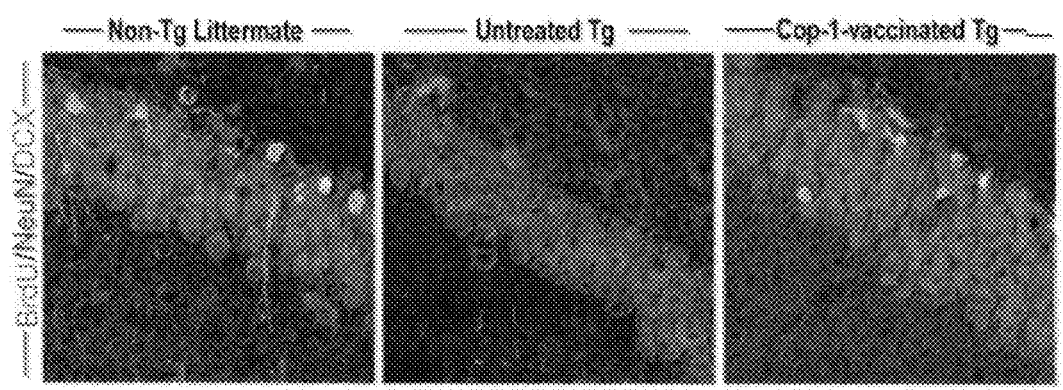
Figure 6E:
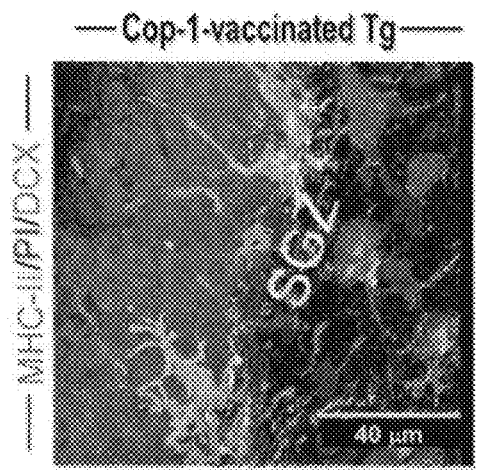

The observed effects of IL-4 on the expression of CD11c, MHC-II, and TNF-α prompted us to examine whether the Cop-1-vaccinated Tg-AD mice would show increased neurogenesis in vivo. Three weeks before tissue excision all mice had been injected with the proliferating-cell marker BrdU, making it possible to detect new neurons. Quantitative analysis of additional sections from the same areas of the hippocampal dentate gyrus disclosed significantly more BrdU$^+$ cells in the Cop-1-vaccinated Tg-AD mice (FIG. 6A) than in their untreated-Tg counterparts. In addition, compared to the numbers of newly formed mature neurons (BrdU$^+$/NeuN$^+$) in their respective non-Tg littermates the numbers were significantly lower in the untreated Tg-AD group, but were similar in the Cop-1-vaccinated Tg-AD group; indicating that the neurogenesis capacity had been at least partially restored by the Cop-1 vaccination (FIG. 6B). Analysis of corresponding sections for DCX, a useful marker for analyzing the absolute number of newly generated pre-mature neurons in the adult dentate gyrus (Rao et al., 2004), disclosed that relative to the non-Tg littermates there were significantly fewer DCX$^+$ cells in the dentate gyri of untreated-Tg-AD mice, and slightly but significantly more in the dentate gyri of Tg-AD mice vaccinated with Cop-1 (FIG. 6C). Confocal micrographs illustrate the differences in the numbers of BrdU$^+$/NeuN$^+$ cells, and in the numbers of DCX$^+$ cells and their dendritic processes, between non-Tg littermates, untreated-Tg-AD mice, and Cop-1-vaccinated Tg-AD mice (FIG. 6D). The results showed that neurogenesis was indeed significantly more abundant in the Cop-1-treated Tg-AD mice than in the untreated-Tg-AD mice. Interestingly, however, in both untreated and Cop-1-vaccinated Tg-AD mice the processes of the DCX-stained neurons in the subgranular zone of the dentate gyrus were short, except in those Cop-1-vaccinated Tg-AD mice in which the DCX$^+$ cells were located adjacent to MHC-II$^+$ microglia (FIG. 6E).

Discussion

We showed here that vaccination of Tg-AD mice with Cop-1 reduced plaque formation and attenuated cognitive decline. Labeling of activated microglia with anti-CD11b antibodies disclosed that staining was heavy in the untreated-Tg-AD mice and significantly less intense in the age-matched Cop-1-vaccinated Tg-AD mice. The decrease in numbers of CD11b$^+$ microglia in Cop-1-vaccinated mice could be an outcome of a reduction in Aβ-plaques, whose deposition in the brain had led to the microglial activation in the first place.

The role of microglia in Alzheimer's disease and other neurodegenerative diseases has been intensively investigated over the last few years, with apparently conflicting results (Streit, 2004). The detection of some CD11b$^+$ microglia in aged wild-type mice that are healthy is in line with the reported age-related increase in activated microglia in the normal human brain (Streit, 2004). It is possible that such microglia are the ones that contribute both to age-related cognitive loss and to impaired neurogenesis (Monje et al., 2003). CD11b were found also in patients with Alzheimer's disease (Akiyama & McGeer, 1990). Although these microglia are phagocytic (Frenkel et al., 2005), they are apparently not efficient enough to fight off the Alzheimer symptoms. In contrast, and in line with our present study, microglia derived from the bone marrow of matched wild-type mice can effectively remove plaques (Simard et al., 2006). These microglia express higher protein levels than are required for antigen presentation and might therefore be more effective phagocytes than the resident microglia. On the basis of our present results, we suggest that the microglia that are needed to support brain maintenance and fight Alzheimer's disease are dendritic-like cells (CD11b$^+$/CD11c$^+$). The CD11c$^+$ microglia might engage in a dialog with T cells that can help to fight off adverse conditions by promoting the buffering of excessive Aβ and supporting both neuronal survival (Butovsky et al., 2005) and neural renewal (Butovsky et al., 2006b). In view of our earlier finding that IL-4, but not IFN-γ, can alter the phenotype of Aβ-committed microglia (Butovsky et al., 2005), it seems likely that the MHC-II$^+$ microglia found adjacent to Aβ plaques in the present study were activated by IL-4. This likelihood is further supported by two of the in-vitro findings of the present study: first, that the Aβ-induced blockage of neurogenesis was partially counteracted by IL-4, either alone or in combination with IFN-γ, but not by IFN-γ alone; and secondly, that the MHC-II$^+$/CD1 microglia which were seen in close proximity to the residual Aβ plaques in the Cop-1-vaccinated Tg-AD mice also expressed IGF-I. Taken together, these findings reinforce the contention that the terms 'beneficial' and 'harmful' cannot be applied in a generalized way to microglial activity (Schwartz et al., 2006).

IL-4 has often been described as an anti-inflammatory cytokine (Chao et al., 1993). Our results strongly argue against this perception and suggest instead that IL-4 activates microglia to adopt a phenotype that seems to acquire a different morphology and a different activity from those of the innately activated microglia or of the activated microglia commonly seen in Alzheimer's disease or in MS. In the latter disease, unlike in Alzheimer's disease, the microglia appear to be overwhelmed by an onslaught of adaptive immunity (Butovsky et al., 2006a). Interestingly, it seems that IL-4 is capable of restoring a favorable activated phenotype even after the microglia have already exhibited phenotypic characteristics of aggregated Aβ ((Butovsky et al., 2005), and the present study), or been overwhelmed by IFN-γ (Butovsky et al., 2006a). Another interesting finding is that LPS and Aβ exhibit similar patterns of MAPK activation in microglia (Pyo et al., 1998). IL-4 can attenuate a MAPK pathway activated by LPS, an effect evidently associated with serine/threonine phosphatase activity (Iribarren et al., 2003). The latter phenomenon might indeed serve as a molecular mechanism underlying the present finding that IL-4 attenuates the detrimental effect of Aβ-activated microglia. Accordingly, we suggest that the activity of IL-4 should not be regarded as anti-inflammatory, but as immunomodulatory.

Based on our in-vitro findings in connection with the effect of IL-4 on microglial phenotype, and the ability of the regimen chosen in the present study to evoke a T-cell response with an IL-4 bias, we suggest that the observed beneficial effect of Cop-1 vaccination on the Tg-AD mice in this study was a result of the evoked T-cell effect on their microglial phenotype.

Example 3

Copolymer-1 Vaccination Counteracts Cognitive Decline in Alzheimer's Disease

Figure 7A:
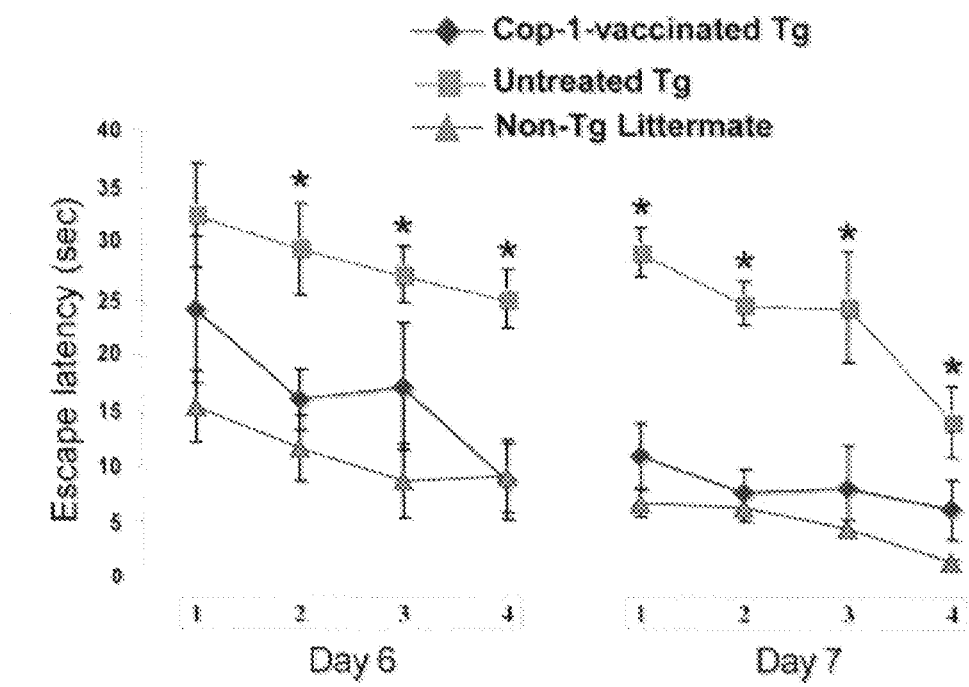
FIGS. 7A-7B show that Cop-1 vaccination counteracts cognitive decline in transgenic (Tg) AD mice. Hippocampus-dependent cognitive activity was tested in the Morris water maze (MWM).
Figure 7B:
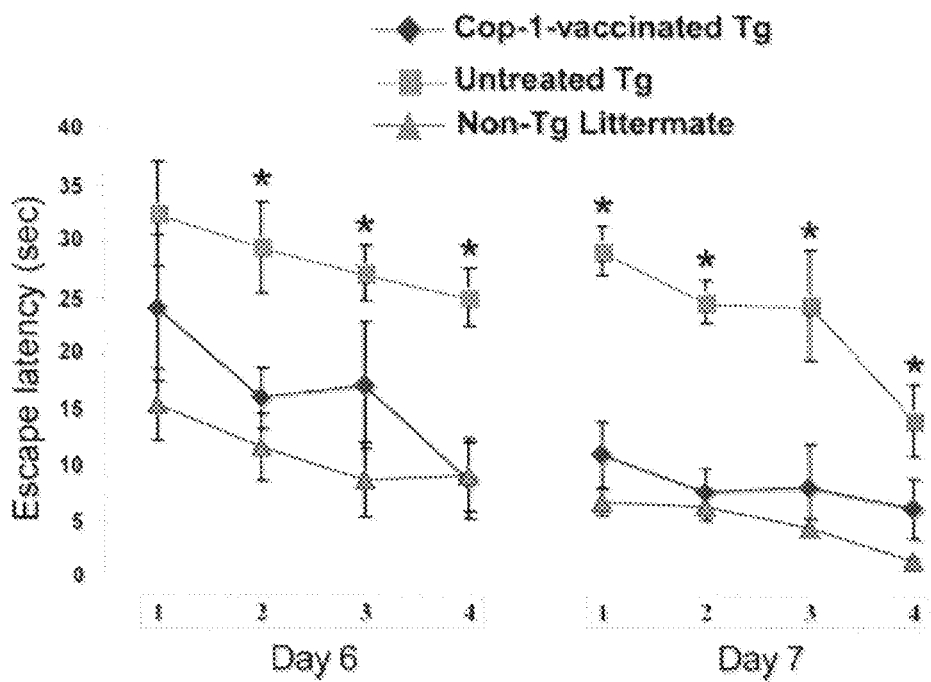
Figure 8A:
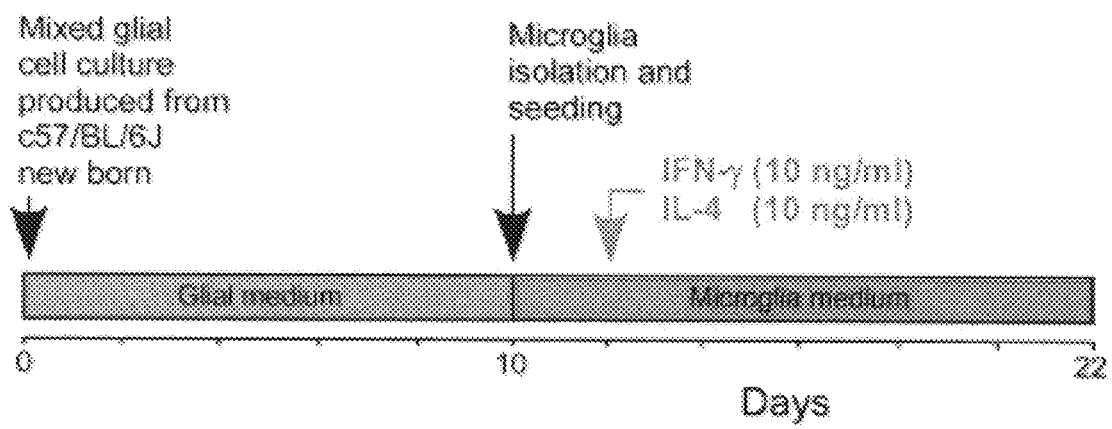
FIGS. 8A-8D show a time course of CD11c expression in microglia activated by IFN-γ and IL-4.
Figure 8B:
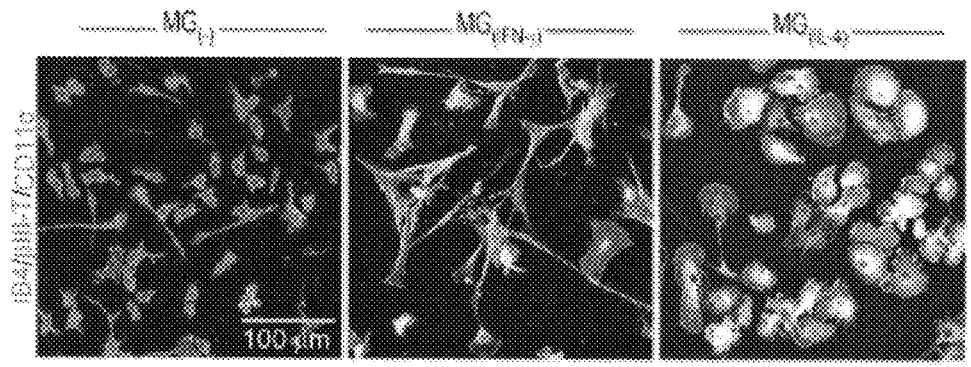
Figure 8C:
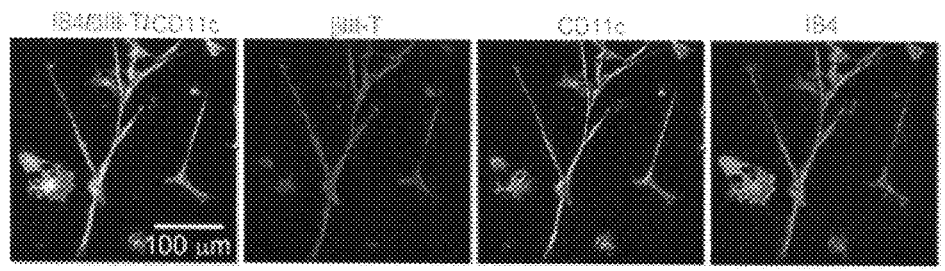
Figure 8D:
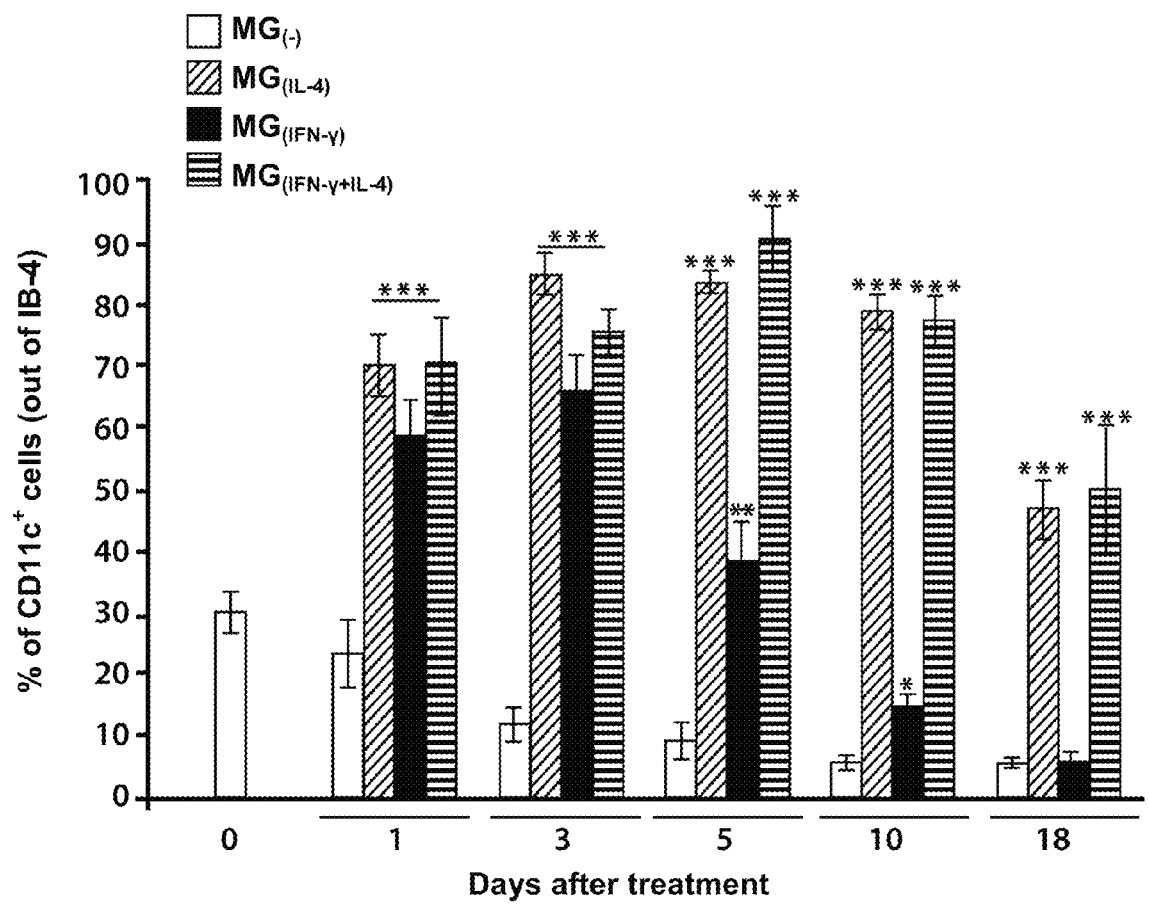

Two weeks before the end of the experiment, all mice were tested in a Morris water maze (MWM) for cognitive activity, as reflected by their performance of a hippocampus-dependent spatial learning/memory task. The MWM performance of the untreated-Tg-AD mice was significantly worse, on average, than that of their age-matched non-Tg littermates (FIGS. 7A-7B). However, the performance of Cop-1-vaccinated Tg-AD mice was superior to that of the untreated-Tg-AD mice and did not differ significantly from that of the non-Tg-AD mice, suggesting that the Cop-1 vaccination had prevented further cognitive loss. Differences in cognitive performance were manifested in both the acquisition (FIG. 7A) and the reversal tasks (FIG. 7B).

The vaccinated mice in this study demonstrated attenuated cognitive loss (tested in a Morris water maze) and increased neurogenesis. These two aspects of hippocampal plasticity are apparently related to the presence of IGF-I and cognitive activity and cell renewal (Butovsky et al., 2006a;b). Reported observations in Tg-AD mice housed in an enriched environment also support a link between mechanisms associated with neurogenesis (Ziv et al., 2006) and with plaque reduction (Lazarov et al., 2005).

Because aggregated Aβ evidently interferes with the ability of microglia to engage in dialog with T cells, its presence in the brain can be expected to cause loss of cognitive ability and impairment of neurogenesis. Homing of CNS-autoreactive T cells to the site of disease or damage in such cases is critical, but will be effective only if those T cells can counterbalance the destructive activity of the aggregated A. As shown here, IFN-γ by itself is impotent against the activity of microglia that are already committed to an aggregated Aβ phenotype, but is effective when added together with IL-4. Thus, the results of this study strongly suggest that the occurrence of neurogenesis in the adult hippocampus depends on well controlled local immune activity associated with microglial production of growth factors such as IGF-I and BDNF (Ziv et al., 2006). In line with this notion is the reported finding that neurogenesis is impaired in animals treated with LPS (Monje et al., 2003), shown to impair microglial production of IGF-I and induce microglial secretion of TNF-α (Butovsky et al., 2005).

Example 4

IFN-γ-Activated Myeloid Cells and their Uses for Promoting Tissue Repair, Detection of and Delivery of Drugs to Damaged Tissue We have shown that when IFN-γ was added in combination with IL-4 their effect in counteracting the negative activity of Aβ-activated microglia on NPC survival and differentiation was stronger than the effect of IL-4 alone (FIG. 1B). However, our data demonstrates that IFN-γ alone, similarly to IL-4 but transiently, induces CD11c if the cells are treated with IFN-γ in a narrow concentration range of up to 20 ng/ml, induces neuroprotection (Butovsky et al., 2005) and is able to support neurogenesis from neural stem/progenitor cells (Butovsky et al., 2006b). CD11c is upregulated and reach the peak at 2-3 days after IFN-γ activation in microglia (FIGS. 8A-8D) or bone-marrow-derived myeloid cells (data not shown). Thus, upregulation of CD11c on bone marrow derived myeloid cells by IFN-γ will allow the cells to reach injured sites and induce beneficial effect.

Example 5

Weekly Vaccination with Copaxone as a Potential Therapy for Dry Age-Related Macular Degeneration The results of the previous examples showed that vaccination of Tg-AD mice with Cop-1 in a regimen previously found to lead to neuroprotection resulted in a microglial phenotype switch from CD11b$^+$ to CD11b$^+$/CD11c$^+$, and that this was correlated with plaque removal, neurogenesis, and attenuated cognitive loss. The beneficial effect was attributed to a phenotype switch of the infiltrating microglia as well as to recruitment of blood-borne monocytes.

Based on these findings and on the many features common between Alzheimer's disease and AMD, we hypothesized that in AMD, similar to Alzheimer's disease, weekly Cop-1 treatment would likely lead to clearing of drusen and this, subsequently, may restrain the progression of dry to wet AMD. It should be emphasized that Cop-1 given in different regimens results in different therapies; daily treatment has no beneficial effects in paradigms of neurodegenerative diseases, but is effective in suppressing inflammatory disease in patients like multiple sclerosis. Therefore, we decided to embark on a clinical trial with AMD patients in a protocol of weekly administration.

The natural fate of drusen in our population of patients was examined by analysis of fundus photographs of unenrolled and untreated dry AMD patients. These patients comprised an observational group.

The effect of Cop-1 (Copaxone®, Teva) on drusen was examined during a prospective, pilot, randomized, double-masked, placebo-controlled, comparative trial. Patients over 50 years of age with intermediate dry AMD in both eyes were enrolled.

Enrolled patients were randomly (ratio 2 to 1) treated either with subcutaneous injections of Copaxone (20 mg) or placebo injections on a weekly basis for a period of 12 weeks. Complete eye examination, along with fundus photography, was performed at baseline, 6- and 12-week visits. The primary outcome was the change in total drusen area and it was calculated using Image-Pro software. Analysis of patients from the observational group (17 eyes) showed an increase of 25.2% in total drusen area.

At 12 week, 8 eyes treated with Copaxone showed a reduction in total drusen area from baseline of 53.6% (range, 5-89%). Two eyes receiving placebo injections demonstrated reduction of 0.6% in total drusen area.

This study thus shows a potential beneficial effect for Copaxone for treating AMD. Due to the limited numbers of the enrolled patients, no statistical significant conclusion can be drawn. Yet, the results justify and encourage to extend and continue this study for fighting off drusens. In light of the underlying mechanism of weekly treatment with Copaxone in animal models of neurodegenerative diseases, its effect on AMD might be beyond the drusens' elimination in protecting neurons and promoting repair.

REFERENCES

Akiyama, H., Barger, S., Barnum, S., Bradt, B., Bauer, J., Cole, G M., Cooper, N R, Eikelenboom, P., Emmerling, M., Fiebich, B L., Finch, C E, Frautschy, S., Griffin, W S., Hampel, H., Hull, M. et al. Inflammation and Alzheimer's disease. *Neurobiol Aging* 21, 383-421 (2000).

Akiyama, H & McGeer, P L. Brain microglia constitutively express beta-2 integrins. *J Neuroimmunol* 30, 81-93 (1990).

Ambati, J. et al. An animal model of age-related macular degeneration in senescent Ccl-2- or Ccr-2-deficient mice. *Nat Med* 9, 1390-7 (2003).

Angelov, D N, Waibel, S, Guntinas-Lichius, O, Lenzen, M, Neiss, W F, Tomov, T L, Yoles, E, Kipnis, J, Schori, H, Reuter, A, Ludolph A, and Schwartz, M. Therapeutic vaccine for acute and chronic motor neuron diseases: Implications for amyotrophic lateral sclerosis. *Proc Natl Acad Sci USA* 100, 4790-5 (2003).

Avidan, H, Kipnis, J, Butovsky, O, Caspi, R R & Schwartz, M. Vaccination with autoantigen protects against aggregated beta-amyloid and glutamate toxicity by controlling microglia: effect of CD4+CD25+ T cells. *Eur J Immunol* 34, 3434-45 (2004).

Bakalash, S, Shlomo, G B, Aloni, E, Shaked, I, Wheeler, L, Ofri, R & Schwartz, M. T cell-based vaccination for morphological and functional neuroprotection in a rat model of chronically elevated intraocular pressure. *J Mol Med* 83, 904-16 (2005).

Bakalash, S, Kessler, A, Mizrahi, T, Nussenblatt, R & Schwartz, M. Antigenic specificity of immunoprotective therapeutic vaccination for glaucoma. *Invest. Opthalmol. Vis. Sci.* 44, 3374-81 (2003).

Bard, F, Cannon, C, Barbour, R, Burke, R L, Games, D, Grajeda, H, Guido, T, Hu, K, Huang, J, Johnson-Wood, K. et al. Peripherally administered antibodies against amyloid beta-peptide enter the central nervous system and reduce pathology in a mouse model of Alzheimer disease. *Nat Med* 6, 916-9 (2000).

Barouch, R. & Schwartz, M. Autoreactive T cells induce neurotrophin production by immune and neural cells in injured rat optic nerve: implications for protective autoimmunity. *Faseb J* 16, 1304-6 (2002).

Borchelt, D R, Ratovitski, T, van Lare, J, Lee, M K, Gonzales, V, Jenkins, N A, Copeland, N G, Price, D L & Sisodia, S S. Accelerated amyloid deposition in the brains of transgenic mice co-expressing mutant presenilin 1 and amyloid precursor proteins. *Neuron* 19, 939-45 (1997).

Butovsky, O., M. Koronyo-Hamaoui, G. Kunis, E. Ophir, G. Landa, H. Cohen & M. Schwartz. Glatiramer acetate fights against Alzheimer's disease by inducing dendritic-like microglia expressing insulin-like growth factor-1. 2006 Jul. 24 [Epub ahead of print] (2006a)

Butovsky, O, Ziv, Y, Schwartz, A, Landa, G, Talpalar, A E, Pluchino, S, Martino, G & Schwartz, M. Microglia activated by IL-4 or IFN-gamma differentially induce neurogenesis and oligodendrogenesis from adult stem/progenitor cells. *Mol Cell Neurosci* 31, 149-60 (2006b).

Butovsky, O, Landa, G, Kunis, G, Ziv, Y, Avidan, H, Greenberg, N, Schwartz, A, Smirnov, I, Pollack, A, Jung, S & Schwartz, M. Induction and blockage of oligodendrogenesis by differently activated microglia in an animal model of multiple sclerosis. *J Clin Invest* 116:905-15 (2006c).

Butovsky, O, Talpalar, A E, Ben-Yaakov, K & Schwartz, M. Activation of microglia by aggregated beta-amyloid or lipopolysaccharide impairs MHC-II expression and renders them cytotoxic whereas IFN-gamma and IL-4 render them protective. *Mol Cell Neurosci* 29, 381-93 (2005).

Butovsky, O, Hauben, E & Schwartz, M. Morphological aspects of spinal cord autoimmune neuroprotection: colocalization of T cells with B7-2 (CD86) and prevention of cyst formation. *Faseb J.* 15, 1065-7 (2001).

Chao, C C, Molitor, T W & Hu, S, Neuroprotective role of IL-4 against activated microglia. *J Immunol* 151, 1473-81 (1993).

Frenkel, D, Maron, R, Burt, D S & Weiner, H L. Nasal vaccination with a proteosome-based adjuvant and glatiramer acetate clears beta-amyloid in a mouse model of Alzheimer disease. *J Clin Invest* 115, 2423-2433 (2005).

Furlan, R. et al. Vaccination with amyloid-beta peptide induces autoimmune encephalomyelitis in C57/BL6 mice. *Brain* 126, 285-91 (2003).

Gupta, N, Brown, K E & Milam, A H. Activated microglia in human retinitis pigmentosa, late-onset retinal degeneration, and age-related macular degeneration. *Exp Eye Res* 76, 463-71 (2003).

Hageman, G S. & Mullins, R F. Molecular composition of drusen as related to substructural phenotype. *Mol Vis* 5, 28 (1999).

Hageman, G S. et al. An integrated hypothesis that considers drusen as biomarkers of immune-mediated processes at the RPE-Bruch's membrane interface in aging and age-related macular degeneration. *Prog Retin Eye Res* 20, 705-32 (2001).

Hardy, J. & Selkoe, D J. The amyloid hypothesis of Alzheimer's disease: progress and problems on the road to therapeutics. *Science* 297, 353-6 (2002).

Haughey, N J, Nath, A, Chan, S L, Borchard, A C, Rao, M S & Mattson, M P. Disruption of neurogenesis by amyloid beta-peptide, and perturbed neural progenitor cell homeostasis, in models of Alzheimer's. *J Neurochem* 83, 1509-24 (2002).

Holz, F G. et al. Bilateral macular drusen in age-related macular degeneration. Prognosis and risk factors. *Opthalmology* 101, 1522-8 (1994).

Iribarren, P, Cui, Y H, Le, Y, Ying, G, Zhang, X, Gong, W & Wang, J M. *J Immunol* 171, 5482-8 (2003).

Jankowsky, J. L., Fadale, D. J., Anderson, J., Xu, G. M., Gonzales, V., Jenkins, N. A., Copeland, N. G., Lee, M. K., Younkin, L. H., Wagner, S. L. et al. Mutant presenilins specifically elevate the levels of the 42 residue beta-amyloid peptide in vivo: evidence for augmentation of a 42-specific gamma secretase. *Hum Mol Genet* 13, 159-70 (2004).

Jin, K, Galvan, V, Xie, L, Mao, X O, Gorostiza, O F, Bredesen, D E & Greenberg, D A. Enhanced neurogenesis in Alzheimer's disease transgenic (PDGF-APPSw,Ind) mice. *Proc Natl Acad Sci USA* 101, 13363-7 (2004a).

Jin, K, Peel, A L, Mao, X O, Xie, L, Cottrell, B A, Henshall, D C & Greenberg, D A. Increased hippocampal neurogenesis in Alzheimer's disease. *Proc Natl Acad Sci USA* 101, 343-7 (2004b).

Kerschensteiner, M, Gallmeier, E, Behrens, L, Leal, V V, Misgeld, T, Klinkert, W E, Kolbeck, R, Hoppe, E, Oropeza-Wekerle, R L, Bartke, I. et al. Activated human T cells, B cells, and monocytes produce brain-derived neurotrophic factor in vitro and in inflammatory brain lesions: a neuroprotective role of inflammation? *J. Exp. Med.* 189, 865-70 (1999).

Kipnis, J. & Schwartz, M. Dual action of glatiramer acetate (Cop-1) in the treatment of CNS autoimmune and neurodegenerative disorders. *Trends Mol Med* 8, 319-23 (2002).

Kipnis, J, Avidan, H, Caspi, R R & Schwartz, M. Dual effect of CD4+CD25+ regulatory T cells in neurodegeneration: Pro- and anti-inflammatory cytokines determine microglial activity. *Proc. Natl. Acad. Sci. USA* 101 Suppl 2, 14663-14669 (2004a).

Kipnis, J., Cohen, H., Cardon, M., Ziv, Y. & Schwartz, M. (2004b) *Proc Natl Acad Sci USA* 101, 8180-5.

Kipnis, J, Mizrahi, T, Hauben, E, Shaked, I, Shevach, E & Schwartz, M. Neuroprotective autoimmunity: naturally occurring CD4+CD25+ regulatory T cells suppress the ability to withstand injury to the central nervous system. *Proc Natl Acad Sci USA* 99, 15620-5 (2002).

Kipnis, J, Yoles, E, Porat, Z, Cohen, A, Mor, F, Sela, M, Cohen, I R & Schwartz, M. T cell immunity to copolymer 1 confers neuroprotection on the damaged optic nerve: possible therapy for optic neuropathies. *Proc. Natl. Acad. Sci. USA* 97, 7446-51 (2000).

Klayer, C. C. et al. Is age-related maculopathy associated with Alzheimer's Disease? The Rotterdam Study. *Am J Epidemiol* 150, 963-8 (1999).

Klein R, Klein B E, Linton K L. Prevalence of age-related maculopathy. The Beaver Dam Eye Study. *Opthalmology* 99:933-43 (1992).

Kliffen, M., de Jong, P T & Luider, T M. Protein analysis of human maculae in relation to age-related maculopathy. *Lab Invest* 73, 267-72 (1995).

Lazarov, O., Robinson, J., Tang, Y. P., Hairston, I. S., Korade-Mirnics, Z., Lee, V. M., Hersh, L. B., Sapolsky, R. M., Mimics, K. & Sisodia, S. S. *Cell* 120, 701-13 (2005).

Lichtenwalner, R. J., Forbes, M. E., Bennett, S. A., Lynch, C. D., Sonntag, W. E. & Riddle, D. R. (2001) Neuroscience 107, 603-13.

Luibl, V. et al. Drusen deposits associated with aging and age-related macular degeneration contain nonfibrillar amyloid oligomers. *J Clin Invest* 116, 378-85 (2006).

Mitchell P, Smith W, Attebo K, Wang J J. Prevalence of age-related maculopathy in Australia. The Blue Mountains Eye Study. *Opthalmology* 102:1450-60 (1995).

Mizrahi, T, Hauben, E & Schwartz, M. The tissue-specific self-pathogen is the protective self-antigen: the case of uveitis. *J. Immunol.* 169, 5971-7 (2002).

Moalem, G. et al. Production of neurotrophins by activated T cells: implications for neuroprotective autoimmunity. *J. Autoimmun.* 15, 331-45 (2000).

Moalem, G, Leibowitz-Amit, R, Yoles, E, Mor, F, Cohen, I R & Schwartz, M. Autoimmune T cells protect neurons from secondary degeneration after central nervous system axotomy. *Nat. Med.* 5, 49-55 (1999).

Monje, M L, Toda, H. & Palmer, T D. Inflammatory blockade restores adult hippocampal neurogenesis. *Science* 302, 1760-5 (2003).

Monsonego, A, Imitola, J, Petrovic, S, Zota, V, Nemirovsky, A, Baron, R, Fisher, Y, Owens, T & Weiner, H. L. A{beta}-induced meningoencephalitis is IFN-{gamma}-dependent and is associated with T cell-dependent clearance of A{beta} in a mouse model of Alzheimer's disease. *Proc Natl Acad Sci USA,* 103:5048-53 (2006).

Morgan, D. et al. A beta peptide vaccination prevents memory loss in an animal model of Alzheimer's disease. *Nature* 408, 982-5 (2000).

Morita Y, Yang J, Gupta R, Shimizu K, Shelden E A, Endres J, Mule J J, McDonagh K T, Fox D A. Dendritic cells genetically engineered to express IL-4 inhibit murine collagen-induced arthritis. *J Clin Invest* 107(10):1275-84. (2001)

Mullins, R F, Russell, S R, Anderson, D H & Hageman, G S. Drusen associated with aging and age-related macular degeneration contain proteins common to extracellular deposits associated with atherosclerosis, elastosis, amyloidosis, and dense deposit disease. *Faseb J* 14, 835-46 (2000).

Nimmerjahn, A, Kirchhoff, F & Helmchen, F. Resting microglial cells are highly dynamic surveillants of brain parenchyma in vivo. *Science* 308, 1314-8 (2005).

Penfold, P L, Madigan, M C & Provis, S M. Antibodies to human leucocyte antigens indicate subpopulations of microglia in human retina. *Vis Neurosci* 7, 383-8 (1991).

Pluchino, S, Quattrini, A, Brambilla, E, Gritti, A, Salani, G, Dina, G, Galli, R, Del Carro, U, Amadio, S, Bergami, A. et al. Injection of adult neurospheres induces recovery in a chronic model of multiple sclerosis. *Nature* 422, 688-94 (2003).

Provis, J M. Development of the primate retinal vasculature. *Prog Retin Eye Res* 20, 799-821 (2001).

Pyo, H., Jou, I., Jung, S., Hong, S. & Joe, E H *Neuroreport* 9, 871-4 (1998).

Rao, M. S. & Shetty, A. K. *Eur J Neurosci* 19, 234-46 (2004).

Roque, R S, Rosales, A A, Jingjing, L, Agarwal, N & Al-Ubaidi, M R. Retina-derived microglial cells induce photoreceptor cell death in vitro. *Brain Res* 836, 110-9 (1999).

Schori, H, Kipnis, J, Yoles, E, WoldeMussie, E, Ruiz, G, Wheeler, L A & Schwartz, M. Vaccination for protection of retinal ganglion cells against death from glutamate cytotoxicity and ocular hypertension: implications for glaucoma. *Proc. Natl. Acad. Sci. USA* 98, 3398-403 (2001).

Schwartz, M, Butovsky, O, Bruck, W & Hanisch, U K. Microglial phenotype: is the commitment reversible? *Trends Neurosci* 29, 68-74 (2006).

Selkoe, D J. The molecular pathology of Alzheimer's disease. *Neuron* 6, 487-98 (1991).

Shaked, I, Porat, Z, Gersner, R, Kipnis, J. & Schwartz, M. Early activation of microglia as antigen-presenting cells correlates with T cell-mediated protection and repair of the injured central nervous system. *J Neuroimmunol* 146, 84-93 (2004).

Shaked, I, Tchoresh, D, Gersner, R, Meiri, G, Mordechai, S, Xiao, X, Hart, R P. & Schwartz, M. Protective autoimmunity: interferon-gamma enables microglia to remove glutamate without evoking inflammatory mediators. *J Neurochem* 92, 997-1009 (2005).

Simard, A R, Soulet, D, Gowing, G, Julien, J P & Rivest, S. Bone marrow-derived microglia play a critical role in restricting senile plaque formation in Alzheimer's disease. *Neuron* 49, 489-502 (2006).

Streilein, J W, Wilbanks, G A & Cousins, S W. Immunoregulatory mechanisms of the eye. *J Neuroimmunol* 39, 185-200 (1992).

Streit, W J. Microglia and Alzheimer's disease pathogenesis. *J Neurosci Res* 77, 1-8 (2004).

Teitelbaum, D., Fridkis-Hareli, M., Amon, R. & Sela, M. *J Neuroimmunol* 64, 209-17 (1996).

Yin, Y. et al. Macrophage-derived factors stimulate optic nerve regeneration. *J. Neurosci.* 23, 2284-93 (2003).

Yoles, E, Hauben, E, Palgi, O, Agranov, E, Gothilf, A, Cohen, A, Kuchroo, V, Cohen, I R, Weiner, H & Schwartz, M. Protective autoimmunity is a physiological response to CNS trauma. *J Neurosci* 21, 3740-8 (2001).

Yoshida, T. et al. The potential role of amyloid beta in the pathogenesis of age-related macular degeneration. *J Clin Invest* 115, 2793-800 (2005).

Ziemssen, T, Kumpfel, T, Klinkert, W E, Neuhaus, O & Hohlfeld, R. Glatiramer acetate-specific T-helper 1- and 2-type cell lines produce BDNF: implications for multiple sclerosis therapy. Brain-derived neurotrophic factor. *Brain* 125, 2381-91 (2002).

Ziv, Y, Ron, N, Butovsky, O, Landa, G, Sudai, E, Greenberg, N, Cohen, H, Kipnis, J & Schwartz, M. Immune cells contribute to the maintenance of neurogenesis and spatial learning abilities in adulthood. *Nat Neurosci* 9, 268-75 (2006).

The invention claimed is:

1. A method for reducing drusen area in an individual with age-related macular degeneration, which comprises causing T cells that produce IL-4 to accumulate in the eye of said individual by administering to said individual an agent selected from the group consisting of Copolymer 1; a Copolymer 1-related peptide; a Copolymer 1-related polypeptide; and T cells activated against Copolymer 1, a Copolymer 1-related peptide or a Copolymer 1-related polypeptide, thereby reducing drusen area in said individual.

2. The method according to claim 1, wherein said agent is Copolymer 1.

3. The method according to claim 1, wherein said agent is T cells activated by Copolymer 1.

4. The method according to claim 1, wherein said age-related macular degeneration is dry age-related macular degeneration.

* * * * *

SEQUENCE LISTING

```
<160> NUMBER OF SEQ ID NOS: 51

<210> SEQ ID NO 1
<211> LENGTH: 15
<212> TYPE: PRT
<213> ORGANISM: Artificial
<220> FEATURE:
<223> OTHER INFORMATION: Synthetic peptide

<400> SEQUENCE: 1

Ala Ala Ala Tyr Ala Ala Ala Ala Ala Ala Lys Ala Ala Ala Ala
```

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Ala Lys Glu Tyr Ala Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide

<400> SEQUENCE: 4

Ala Lys Lys Tyr Ala Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5

Ala Glu Ala Tyr Ala Ala Ala Ala Ala Ala Lys Ala Ala Ala Ala
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Lys Glu Ala Tyr Ala Ala Ala Ala Ala Ala Lys Ala Ala Ala Ala
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

Ala Glu Glu Tyr Ala Ala Ala Ala Ala Ala Lys Ala Ala Ala Ala
1               5                   10                  15

```
<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Ala Ala Glu Tyr Ala Ala Ala Ala Ala Lys Ala Ala Ala Ala Ala
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala Ala
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Ala Ala Lys Tyr Glu Ala Ala Ala Ala Lys Ala Ala Ala Ala Ala
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala Ala
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala Ala
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala Ala
1               5                   10                  15
```

<210> SEQ ID NO 14
<211> LENGTH: 15
<212> TYPE: PRT
<213> ORGANISM: Artificial
<220> FEATURE:
<223> OTHER INFORMATION: Synthetic peptide

<400> SEQUENCE: 14

```
Glu Ala Lys Tyr Ala Ala Ala Ala Ala Lys Ala Ala Ala Ala Ala
1               5                   10                  15
```

<210> SEQ ID NO 15
<211> LENGTH: 15
<212> TYPE: PRT
<213> ORGANISM: Artificial
<220> FEATURE:
<223> OTHER INFORMATION: Synthetic peptide

<400> SEQUENCE: 15

```
Ala Glu Lys Tyr Ala Ala Ala Ala Ala Ala Ala Ala Ala Ala Ala
1               5                   10                  15
```

<210> SEQ ID NO 16
<211> LENGTH: 15
<212> TYPE: PRT
<213> ORGANISM: Artificial
<220> FEATURE:
<223> OTHER INFORMATION: Synthetic peptide

<400> SEQUENCE: 16

```
Ala Lys Glu Tyr Ala Ala Ala Ala Ala Ala Ala Ala Ala Ala Ala
1               5                   10                  15
```

<210> SEQ ID NO 17
<211> LENGTH: 15
<212> TYPE: PRT
<213> ORGANISM: Artificial
<220> FEATURE:
<223> OTHER INFORMATION: Synthetic peptide

<400> SEQUENCE: 17

```
Ala Lys Lys Tyr Glu Ala Ala Ala Ala Ala Ala Ala Ala Ala Ala
1               5                   10                  15
```

<210> SEQ ID NO 18
<211> LENGTH: 15
<212> TYPE: PRT
<213> ORGANISM: Artificial
<220> FEATURE:
<223> OTHER INFORMATION: Synthetic peptide

<400> SEQUENCE: 18

```
Ala Lys Lys Tyr Ala Glu Ala Ala Ala Ala Ala Ala Ala Ala Ala
1               5                   10                  15
```

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

```
Ala Glu Ala Tyr Lys Ala Ala Ala Ala Ala Ala Ala Ala Ala Ala
1               5                   10                  15
```

```
<210> SEQ ID NO 20
<211> LENGTH: 15
<212> TYPE: PRT
<213> ORGANISM: Artificial
<220> FEATURE:
<223> OTHER INFORMATION: Synthetic peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
```

```
<211> LENGTH: 15
<212> TYPE: PRT
<213> ORGANISM: Artificial
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
```

```
<212> TYPE: PRT
<213> ORGANISM: Artificial
<220> FEATURE:
<223> OTHER INFORMATION: Synthetic peptide

<400> SEQUENCE: 32
```

Ala Lys Tyr Ala Glu Ala Ala Ala Ala Ala Ala Ala Ala
1               5                   10                  15

```
<210> SEQ ID NO 33
<211> LENGTH: 1247
<212> TYPE: PRT
<213> ORGANISM: Homo sapiens

<400> SEQUENCE: 33
```

Met Met Arg Glu Trp Val Leu Leu Met Ser Val Leu Leu Cys Gly Leu
1               5                   10                  15

Ala Gly Pro Thr His Leu Phe Gln Pro Ser Leu Val Leu Asp Met Ala
                20                  25                  30

Lys Val Leu Leu Asp Asn Tyr Cys Phe Pro Glu Asn Leu Leu Gly Met
        35                  40                  45

Gln Glu Ala Ile Gln Gln Ala Ile Lys Ser His Glu Ile Leu Ser Ile
    50                  55                  60

Ser Asp Pro Gln Thr Leu Ala Ser Val Leu Thr Ala Gly Val Gln Ser
65                  70                  75                  80

Ser Leu Asn Asp Pro Arg Leu Val Ile Ser Tyr Glu Pro Ser Thr Pro
                85                  90                  95

Glu Pro Pro Pro Gln Val Pro Ala Leu Thr Ser Leu Ser Glu Glu Glu
                100                 105                 110

Leu Leu Ala Trp Leu Gln Arg Gly Leu Arg His Glu Val Leu Glu Gly
            115                 120                 125

Asn Val Gly Tyr Leu Arg Val Asp Ser Val Pro Gly Gln Glu Val Leu
130                 135                 140

Ser Met Met Gly Glu Phe Leu Val Ala His Val Trp Gly Asn Leu Met
145                 150                 155                 160

Gly Thr Ser Ala Leu Val Leu Asp Leu Arg His Cys Thr Gly Gly Gln
                165                 170                 175

Val Ser Gly Ile Pro Tyr Ile Ile Ser Tyr Leu His Pro Gly Asn Thr
            180                 185                 190

Ile Leu His Val Asp Thr Ile Tyr Asn Arg Pro Ser Asn Thr Thr Thr
        195                 200                 205

Glu Ile Trp Thr Leu Pro Gln Val Leu Gly Glu Arg Tyr Gly Ala Asp
    210                 215                 220

Lys Asp Val Val Val Leu Thr Ser Ser Gln Thr Arg Gly Val Ala Glu
225                 230                 235                 240

Asp Ile Ala His Ile Leu Lys Gln Met Arg Arg Ala Ile Val Val Gly
                245                 250                 255

Glu Arg Thr Gly Gly Gly Ala Leu Asp Leu Arg Lys Leu Arg Ile Gly
            260                 265                 270

Glu Ser Asp Phe Phe Phe Thr Val Pro Val Ser Arg Ser Leu Gly Pro
        275                 280                 285

Leu Gly Gly Gly Ser Gln Thr Trp Glu Gly Ser Gly Val Leu Pro Cys
    290                 295                 300

Val Gly Thr Pro Ala Glu Gln Ala Leu Glu Lys Ala Leu Ala Ile Leu
305                 310                 315                 320

Thr Leu Arg Ser Ala Leu Pro Gly Val Val His Cys Leu Gln Glu Val

```
                   325                 330                 335
Leu Lys Asp Tyr Tyr Thr Leu Val Asp Arg Val Pro Thr Leu Leu Gln
                340                 345                 350

His Leu Ala Ser Met Asp Phe Ser Thr Val Val Ser Glu Glu Asp Leu
                355                 360                 365

Val Thr Lys Leu Asn Ala Gly Leu Gln Ala Ala Ser Glu Asp Pro Arg
                370                 375                 380

Leu Leu Val Arg Ala Ile Gly Pro Thr Glu Thr Pro Ser Trp Pro Ala
385                 390                 395                 400

Pro Asp Ala Ala Ala Glu Asp Ser Pro Gly Val Ala Pro Glu Leu Pro
                405                 410                 415

Glu Asp Glu Ala Ile Arg Gln Ala Leu Val Asp Ser Val Phe Gln Val
                420                 425                 430

Ser Val Leu Pro Gly Asn Val Gly Tyr Leu Arg Phe Asp Ser Phe Ala
                435                 440                 445

Asp Ala Ser Val Leu Gly Val Leu Ala Pro Tyr Val Leu Arg Gln Val
                450                 455                 460

Trp Glu Pro Leu Gln Asp Thr Glu His Leu Ile Met Asp Leu Arg His
465                 470                 475                 480

Asn Pro Gly Gly Pro Ser Ser Ala Val Pro Leu Leu Ser Tyr Phe
                485                 490                 495

Gln Gly Pro Glu Ala Gly Pro Val His Leu Phe Thr Thr Tyr Asp Arg
                500                 505                 510

Arg Thr Asn Ile Thr Gln Glu His Phe Ser His Met Glu Leu Pro Gly
                515                 520                 525

Pro Arg Tyr Ser Thr Gln Arg Gly Val Tyr Leu Leu Thr Ser His Arg
                530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
                580                 585                 590

Val Pro Val Leu Thr Phe Ile Asp Asn His Gly Glu Ala Trp Leu Gly
                595                 600                 605

Gly Gly Val Val Pro Asp Ala Ile Val Leu Ala Glu Glu Ala Leu Asp
                610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

Val Gly Gln Thr Ser Ala Leu Leu Arg Ala Lys Leu Ala Gln Gly Ala
                660                 665                 670

Tyr Arg Thr Ala Val Asp Leu Glu Ser Leu Ala Ser Gln Leu Thr Ala
                675                 680                 685

Asp Leu Gln Glu Val Ser Gly Asp His Arg Leu Leu Val Phe His Ser
                690                 695                 700

Pro Gly Glu Leu Val Val Glu Glu Ala Pro Pro Pro Pro Ala Val
705                 710                 715                 720

Pro Ser Pro Glu Glu Leu Thr Tyr Leu Ile Glu Ala Leu Phe Lys Thr
                725                 730                 735

Glu Val Leu Pro Gly Gln Leu Gly Tyr Leu Arg Phe Asp Ala Met Ala
                740                 745                 750
```

-continued

Glu Leu Glu Thr Val Lys Ala Val Gly Pro Gln Leu Val Arg Leu Val
       755                  760                765

Trp Gln Gln Leu Val Asp Thr Ala Ala Leu Val Ile Asp Leu Arg Tyr
     770                775                780

Asn Pro Gly Ser Tyr Ser Thr Ala Ile Pro Leu Leu Cys Ser Tyr Phe
785                 790                795                800

Phe Glu Ala Glu Pro Arg Gln His Leu Tyr Ser Val Phe Asp Arg Ala
             805                810              815

Thr Ser Lys Val Thr Glu Val Trp Thr Leu Pro Gln Val Ala Gly Gln
          820                825              830

Arg Tyr Gly Ser His Lys Asp Leu Tyr Ile Leu Met Ser His Thr Ser
         835                840              845

Gly Ser Ala Ala Glu Ala Phe Ala His Thr Met Gln Asp Leu Gln Arg
850                 855                860

Ala Thr Val Ile Gly Glu Pro Thr Ala Gly Gly Ala Leu Ser Val Gly
865                 870                875              880

Ile Tyr Gln Val Gly Ser Ser Pro Leu Tyr Ala Ser Met Pro Thr Gln
             885                890              895

Met Ala Met Ser Ala Thr Thr Gly Lys Ala Trp Asp Leu Ala Gly Val
          900                905              910

Glu Pro Asp Ile Thr Val Pro Met Ser Glu Ala Leu Ser Ile Ala Gln
         915                920              925

Asp Ile Val Ala Leu Arg Ala Lys Val Pro Thr Val Leu Gln Thr Ala
     930                935                940

Gly Lys Leu Val Ala Asp Asn Tyr Ala Ser Ala Glu Leu Gly Ala Lys
945                 950                955              960

Met Ala Thr Lys Leu Ser Gly Leu Gln Ser Arg Tyr Ser Arg Val Thr
             965                970              975

Ser Glu Val Ala Leu Ala Glu Ile Leu Gly Ala Asp Leu Gln Met Leu
         980                985              990

Ser Gly Asp Pro His Leu Lys Ala Ala His Ile Pro Glu Asn Ala Lys
     995                1000              1005

Asp Arg Ile Pro Gly Ile Val Pro Met Gln Ile Pro Ser Pro Glu
     1010                1015              1020

Val Phe Glu Glu Leu Ile Lys Phe Ser Phe His Thr Asn Val Leu
    1025                1030              1035

Glu Asp Asn Ile Gly Tyr Leu Arg Phe Asp Met Phe Gly Asp Gly
    1040                1045              1050

Glu Leu Leu Thr Gln Val Ser Arg Leu Leu Val Glu His Ile Trp
    1055                1060              1065

Lys Lys Ile Met His Thr Asp Ala Met Ile Ile Asp Met Arg Phe
    1070                1075              1080

Asn Ile Gly Gly Pro Thr Ser Ser Ile Pro Ile Leu Cys Ser Tyr
    1085                1090              1095

Phe Phe Asp Glu Gly Pro Pro Val Leu Leu Asp Lys Ile Tyr Ser
    1100                1105              1110

Arg Pro Asp Asp Ser Val Ser Glu Leu Trp Thr His Ala Gln Val
    1115                1120              1125

Val Gly Glu Arg Tyr Gly Ser Lys Lys Ser Met Val Ile Leu Thr
    1130                1135              1140

Ser Ser Val Thr Ala Gly Thr Ala Glu Glu Phe Thr Tyr Ile Met
    1145                1150              1155

```
Lys Arg Leu Gly Arg Ala Leu Val Ile Gly Glu Val Thr Ser Gly
    1160                1165                1170

Gly Cys Gln Pro Pro Gln Thr Tyr His Val Asp Asp Thr Asn Leu
    1175                1180                1185

Tyr Leu Thr Ile Pro Thr Ala Arg Ser Val Gly Ala Ser Asp Gly
    1190                1195                1200

Ser Ser Trp Glu Gly Val Gly Val Thr Pro His Val Val Val Pro
    1205                1210                1215

Ala Glu Glu Ala Leu Ala Arg Ala Lys Glu Met Leu Gln His Asn
    1220                1225                1230

Gln Leu Arg Val Lys Arg Ser Pro Gly Leu Gln Asp His Leu
    1235                1240                1245

<210> SEQ ID NO 34
<211> LENGTH: 551
<212> TYPE: PRT
<213> ORGANISM: Bos taurus

<400> SEQUENCE: 34

Val Leu Pro Gly Gln Leu Gly Tyr Leu Arg Phe Asp Ala Met Ala Glu
1               5                   10                  15

Leu Glu Thr Val Lys Ala Val Gly Pro Gln Leu Val Gln Leu Val Trp
            20                  25                  30

Gln Lys Leu Val Asp Thr Ala Ala Leu Val Val Asp Leu Arg Tyr Asn
        35                  40                  45

Pro Gly Ser Tyr Ser Thr Ala Val Pro Leu Leu Cys Ser Tyr Phe Phe
    50                  55                  60

Glu Ala Glu Pro Arg Arg His Leu Tyr Ser Val Phe Asp Arg Ala Thr
65                  70                  75                  80

Ser Arg Val Thr Glu Val Trp Thr Leu Pro His Val Thr Gly Gln Arg
                85                  90                  95

Tyr Gly Ser His Lys Asp Leu Tyr Val Leu Val Ser His Thr Ser Gly
            100                 105                 110

Ser Ala Ala Glu Ala Phe Ala His Thr Met Gln Asp Leu Gln Arg Ala
        115                 120                 125

Thr Ile Ile Gly Glu Pro Thr Ala Gly Gly Ala Leu Ser Val Gly Ile
    130                 135                 140

Tyr Gln Val Gly Ser Ser Ala Leu Tyr Ala Ser Met Pro Thr Gln Met
145                 150                 155                 160

Ala Met Ser Ala Ser Thr Gly Glu Ala Trp Asp Leu Ala Gly Val Glu
                165                 170                 175

Pro Asp Ile Thr Val Pro Met Ser Val Ala Leu Ser Thr Ala Arg Asp
            180                 185                 190

Ile Val Thr Leu Arg Ala Lys Val Pro Thr Val Leu Gln Thr Ala Gly
        195                 200                 205

Lys Leu Val Ala Asp Asn Tyr Ala Ser Pro Glu Leu Gly Val Lys Met
    210                 215                 220

Ala Ala Glu Leu Ser Gly Leu Gln Ser Arg Tyr Ala Arg Val Thr Ser
225                 230                 235                 240

Glu Ala Ala Leu Ala Glu Leu Leu Gln Ala Asp Leu Gln Val Leu Ser
                245                 250                 255

Gly Asp Pro His Leu Lys Thr Ala His Ile Pro Glu Asp Ala Lys Asp
            260                 265                 270

Arg Ile Pro Gly Ile Val Pro Met Gln Ile Pro Ser Pro Glu Val Phe
        275                 280                 285
```

Glu Asp Leu Ile Lys Phe Ser Phe His Thr Asn Val Leu Glu Gly Asn
290                 295                 300

Val Gly Tyr Leu Arg Phe Asp Met Phe Gly Asp Cys Glu Leu Leu Thr
305                 310                 315                 320

Gln Val Ser Glu Leu Leu Val Glu His Val Trp Lys Lys Ile Val His
            325                 330                 335

Thr Asp Ala Leu Ile Val Asp Met Arg Phe Asn Ile Gly Gly Pro Thr
            340                 345                 350

Ser Ser Ile Ser Ala Leu Cys Ser Tyr Phe Phe Asp Glu Gly Pro Pro
        355                 360                 365

Ile Leu Leu Asp Lys Ile Tyr Asn Arg Pro Asn Asp Ser Val Ser Glu
370                 375                 380

Leu Trp Thr Leu Ser Gln Leu Glu Gly Glu Arg Tyr Gly Ser Lys Lys
385                 390                 395                 400

Ser Met Val Ile Leu Thr Ser Thr Leu Thr Ala Gly Ala Ala Glu Glu
                405                 410                 415

Phe Thr Tyr Ile Met Lys Arg Leu Gly Arg Ala Leu Val Ile Gly Glu
                420                 425                 430

Val Thr Ser Gly Gly Cys Gln Pro Pro Gln Thr Tyr His Val Asp Asp
            435                 440                 445

Thr Asp Leu Tyr Leu Thr Ile Pro Thr Ala Arg Ser Val Gly Ala Ala
450                 455                 460

Asp Gly Ser Ser Trp Glu Gly Val Gly Val Val Pro Asp Val Ala Val
465                 470                 475                 480

Pro Ala Glu Ala Ala Leu Thr Arg Ala Gln Glu Met Leu Gln His Thr
                485                 490                 495

Pro Leu Arg Ala Arg Arg Ser Pro Arg Leu His Gly Arg Arg Lys Gly
                500                 505                 510

His Gln Gln Gln Ser Gln Gly Arg Ala Gly Ser Leu Gly Arg Asn Gln
            515                 520                 525

Gly Val Val Arg Pro Glu Val Leu Thr Glu Ala Pro Ser Gly Gln Lys
530                 535                 540

Arg Gly Leu Leu Gln Cys Gly
545                 550

<210> SEQ ID NO 35
<211> LENGTH: 405
<212> TYPE: PRT
<213> ORGANISM: Homo sapiens

<400> SEQUENCE: 35

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
            35                  40                  45

Val Leu Val Asp Pro Asp Leu Val Lys Gly Lys Lys Val Tyr Val Thr
        50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu

|   |   | 100 |   |   | 105 |   |   | 110 |   |   |   |
|---|---|---|---|---|---|---|---|---|---|---|---|

Lys Lys Leu Gly Ser Asn Thr Tyr Pro Phe Leu Leu Thr Phe Pro Asp
    115     120     125

Tyr Leu Pro Cys Ser Val Met Leu Gln Pro Ala Pro Gln Asp Ser Gly
130     135     140

Lys Ser Cys Gly Val Asp Phe Glu Val Lys Ala Phe Ala Thr Asp Ser
145     150     155     160

Thr Asp Ala Glu Glu Asp Lys Ile Pro Lys Lys Ser Ser Val Arg Leu
     165     170     175

Leu Ile Arg Lys Val Gln His Ala Pro Leu Glu Met Gly Pro Gln Pro
    180     185     190

Arg Ala Glu Ala Ala Trp Gln Phe Phe Met Ser Asp Lys Pro Leu His
   195     200     205

Leu Ala Val Ser Leu Asn Lys Glu Ile Tyr Phe His Gly Glu Pro Ile
210     215     220

Pro Val Thr Val Thr Val Thr Asn Asn Thr Glu Lys Thr Val Lys Lys
225     230     235     240

Ile Lys Ala Phe Val Glu Gln Val Ala Asn Val Val Leu Tyr Ser Ser
    245     250     255

Asp Tyr Tyr Val Lys Pro Val Ala Met Glu Ala Gln Glu Lys Val
    260     265     270

Pro Pro Asn Ser Thr Leu Thr Lys Thr Leu Thr Leu Leu Pro Leu Leu
   275     280     285

Ala Asn Asn Arg Glu Arg Arg Gly Ile Ala Leu Asp Gly Lys Ile Lys
   290     295     300

His Glu Asp Thr Asn Leu Ala Ser Ser Thr Ile Ile Lys Glu Gly Ile
305     310     315     320

Asp Arg Thr Val Leu Gly Ile Leu Val Ser Tyr Gln Ile Lys Val Lys
    325     330     335

Leu Thr Val Ser Gly Phe Leu Gly Glu Leu Thr Ser Ser Glu Val Ala
    340     345     350

Thr Glu Val Pro Phe Arg Leu Met His Pro Gln Pro Glu Asp Pro Ala
   355     360     365

Lys Glu Ser Tyr Gln Asp Ala Asn Leu Val Phe Glu Glu Phe Ala Arg
   370     375     380

His Asn Leu Lys Asp Ala Gly Glu Ala Glu Gly Lys Arg Asp Lys
385     390     395     400

Asn Asp Val Asp Glu
    405

<210> SEQ ID NO 36
<211> LENGTH: 404
<212> TYPE: PRT
<213> ORGANISM: Bos taurus

<400> SEQUENCE: 36

Met Lys Ala Asn Lys Pro Ala Pro Asn His Val Ile Phe Lys Lys Ile
1     5     10     15

Ser Arg Asp Lys Ser Val Thr Ile Tyr Leu Gly Lys Arg Asp Tyr Ile
    20     25     30

Asp His Val Glu Arg Val Glu Pro Val Asp Gly Val Val Leu Val Asp
   35     40     45

Pro Glu Leu Val Lys Gly Lys Arg Val Tyr Val Ser Leu Thr Cys Ala
50     55     60

Phe Arg Tyr Gly Gln Glu Asp Ile Asp Val Met Gly Leu Ser Phe Arg
65                  70                  75                  80

Arg Asp Leu Tyr Phe Ser Gln Val Gln Val Phe Pro Pro Val Gly Ala
            85                  90                  95

Ser Gly Ala Thr Thr Arg Leu Gln Glu Ser Leu Ile Lys Lys Leu Gly
        100                 105                 110

Ala Asn Thr Tyr Pro Phe Leu Leu Thr Phe Pro Asp Tyr Leu Pro Cys
        115                 120                 125

Ser Val Met Leu Gln Pro Ala Pro Gln Asp Val Gly Lys Ser Cys Gly
    130                 135                 140

Val Asp Phe Glu Ile Lys Ala Phe Ala Thr His Ser Thr Asp Val Glu
145                 150                 155                 160

Glu Asp Lys Ile Pro Lys Lys Ser Ser Val Arg Leu Leu Ile Arg Lys
                165                 170                 175

Val Gln His Ala Pro Arg Asp Met Gly Pro Gln Pro Arg Ala Glu Ala
            180                 185                 190

Ser Trp Gln Phe Phe Met Ser Asp Lys Pro Leu Arg Leu Ala Val Ser
    195                 200                 205

Leu Ser Lys Glu Ile Tyr Tyr His Gly Glu Pro Ile Pro Val Thr Val
210                 215                 220

Ala Val Thr Asn Ser Thr Glu Lys Thr Val Lys Ile Lys Val Leu
225                 230                 235                 240

Val Glu Gln Val Thr Asn Val Val Leu Tyr Ser Ser Asp Tyr Tyr Ile
                245                 250                 255

Lys Thr Val Ala Ala Glu Glu Ala Gln Glu Lys Val Pro Pro Asn Ser
            260                 265                 270

Ser Leu Thr Lys Thr Leu Thr Leu Val Pro Leu Leu Ala Asn Asn Arg
    275                 280                 285

Glu Arg Arg Gly Ile Ala Leu Asp Gly Lys Ile Lys His Glu Asp Thr
290                 295                 300

Asn Leu Ala Ser Ser Thr Ile Ile Lys Glu Gly Ile Asp Lys Thr Val
305                 310                 315                 320

Met Gly Ile Leu Val Ser Tyr Gln Ile Lys Val Lys Leu Thr Val Ser
            325                 330                 335

Gly Leu Leu Gly Glu Leu Thr Ser Ser Glu Val Ala Thr Glu Val Pro
        340                 345                 350

Phe Arg Leu Met His Pro Gln Pro Glu Asp Pro Asp Thr Ala Lys Glu
    355                 360                 365

Ser Phe Gln Asp Glu Asn Phe Val Phe Glu Glu Phe Ala Arg Gln Asn
    370                 375                 380

Leu Lys Asp Ala Gly Glu Tyr Lys Glu Glu Lys Thr Asp Gln Glu Ala
385                 390                 395                 400

Ala Met Asp Glu

<210> SEQ ID NO 37
<211> LENGTH: 348
<212> TYPE: PRT
<213> ORGANISM: Homo sapiens

<400> SEQUENCE: 37

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

```
Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
 50                  55                  60

His Lys Lys Leu Arg Thr Pro Leu Asn Tyr Ile Leu Leu Asn Leu Ala
 65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
            115                 120                 125

Val Val Leu Ala Ile Glu Arg Tyr Val Val Cys Lys Pro Met Ser
130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
                180                 185                 190

Thr Leu Lys Pro Glu Val Asn Asn Glu Ser Phe Val Ile Tyr Met Phe
            195                 200                 205

Val Val His Phe Thr Ile Pro Met Ile Ile Ile Phe Phe Cys Tyr Gly
            210                 215                 220

Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
            275                 280                 285

Thr Ile Pro Ala Phe Phe Ala Lys Ser Ala Ala Ile Tyr Asn Pro Val
290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
            340                 345

<210> SEQ ID NO 38
<211> LENGTH: 15
<212> TYPE: PRT
<213> ORGANISM: Artificial
<220> FEATURE:
<223> OTHER INFORMATION: Synthetic peptide

<400> SEQUENCE: 38

Ala Asp Gly Ser Ser Trp Glu Gly Val Gly Val Val Pro Asp Val
1               5                   10                  15

<210> SEQ ID NO 39
<211> LENGTH: 23
<212> TYPE: PRT
<213> ORGANISM: Artificial
<220> FEATURE:
```

<223> OTHER INFORMATION: Synthetic peptide

<400> SEQUENCE: 39

Pro Thr Ala Arg Ser Val Gly Ala Ala Asp Gly Ser Ser Trp Glu Gly
1               5                   10                  15

Val Gly Val Val Pro Asp Val
            20

<210> SEQ ID NO 40
<211> LENGTH: 23
<212> TYPE: PRT
<213> ORGANISM: Artificial
<220> FEATURE:
<223> OTHER INFORMATION: Synthetic peptide

<400> SEQUENCE: 40

His Val Asp Asp Thr Asp Leu Tyr Leu Thr Ile Pro Thr Ala Arg Ser
1               5                   10                  15

Val Gly Ala Ala Asp Gly Ser
            20

<210> SEQ ID NO 41
<211> LENGTH: 8
<212> TYPE: PRT
<213> ORGANISM: Artificial
<220> FEATURE:
<223> OTHER INFORMATION: Synthetic peptide

<400> SEQUENCE: 41

Thr Ser Ser Glu Val Ala Thr Glu
1               5

<210> SEQ ID NO 42
<211> LENGTH: 8
<212> TYPE: PRT
<213> ORGANISM: Artificial
<220> FEATURE:
<223> OTHER INFORMATION: Synthetic peptide

<400> SEQUENCE: 42

Asp Thr Asn Leu Ala Ser Ser Thr
1               5

<210> SEQ ID NO 43
<211> LENGTH: 18
<212> TYPE: PRT
<213> ORGANISM: Artificial
<220> FEATURE:
<223> OTHER INFORMATION: Synthetic peptide

<400> SEQUENCE: 43

Asp Thr Asn Leu Ala Ser Ser Thr Ile Ile Lys Glu Gly Ile Asp Lys
1               5                   10                  15

Thr Val

<210> SEQ ID NO 44
<211> LENGTH: 22
<212> TYPE: PRT
<213> ORGANISM: Artificial
<220> FEATURE:
<223> OTHER INFORMATION: Synthetic peptide

<400> SEQUENCE: 44

Val Pro Leu Leu Ala Asn Asn Arg Glu Arg Arg Gly Ile Ala Leu Asp
1               5                   10                  15

Gly Lys Ile Lys His Glu
            20

<210> SEQ ID NO 45
<211> LENGTH: 20
<212> TYPE: PRT
<213> ORGANISM: Artificial
<220> FEATURE:
<223> OTHER INFORMATION: Synthetic peptide

<400> SEQUENCE: 45

Thr Ser Ser Glu Val Ala Thr Glu Val Pro Phe Arg Leu Met His Pro
1               5                   10                  15

Gln Pro Glu Asp
            20

<210> SEQ ID NO 46
<211> LENGTH: 20
<212> TYPE: PRT
<213> ORGANISM: Artificial
<220> FEATURE:
<223> OTHER INFORMATION: Synthetic peptide

<400> SEQUENCE: 46

Ser Leu Thr Lys Thr Leu Thr Leu Val Pro Leu Leu Ala Asn Asn Arg
1               5                   10                  15

Glu Arg Arg Gly
            20

<210> SEQ ID NO 47
<211> LENGTH: 20
<212> TYPE: PRT
<213> ORGANISM: Artificial
<220> FEATURE:
<223> OTHER INFORMATION: Synthetic peptide

<400> SEQUENCE: 47

Ser Leu Thr Arg Thr Leu Thr Leu Leu Pro Leu Leu Ala Asn Asn Arg
1               5                   10                  15

Glu Arg Ala Gly
            20

<210> SEQ ID NO 48
<211> LENGTH: 21
<212> TYPE: PRT
<213> ORGANISM: Artificial
<220> FEATURE:
<223> OTHER INFORMATION: Synthetic peptide

<400> SEQUENCE: 48

Lys Glu Gly Ile Asp Lys Thr Val Met Gly Ile Leu Val Ser Tyr Gln
1               5                   10                  15

Ile Lys Val Lys Leu
            20

<210> SEQ ID NO 49
<211> LENGTH: 21
<212> TYPE: PRT
<213> ORGANISM: Artificial
<220> FEATURE:
<223> OTHER INFORMATION: Synthetic peptide

<400> SEQUENCE: 49

Lys Glu Gly Ile Asp Arg Thr Val Leu Gly Ile Leu Val Ser Tyr Gln

```
1               5               10              15

Ile Lys Val Lys Leu
                20

<210> SEQ ID NO 50
<211> LENGTH: 8
<212> TYPE: PRT
<213> ORGANISM: Artificial
<220> FEATURE:
<223> OTHER INFORMATION: PEPTIDE 8 ANALOG

<400> SEQUENCE: 50

Thr Ser Ser Glu Ala Ala Thr Glu
1               5

<210> SEQ ID NO 51
<211> LENGTH: 8
<212> TYPE: PRT
<213> ORGANISM: Artificial
<220> FEATURE:
<223> OTHER INFORMATION: Synthetic peptide

<400> SEQUENCE: 51

Asp Thr Ala Leu Ala Ser Ser Thr
1               5
```